(12) United States Patent
Hsu et al.

(10) Patent No.: US 9,249,008 B2
(45) Date of Patent: Feb. 2, 2016

(54) MEMS DEVICE WITH MULTIPLE ELECTRODES AND FABRICATING METHOD THEREOF

(71) Applicant: INDUSTRIAL TECHNOLOGY RESEARCH INSTITUTE, Hsinchu (TW)

(72) Inventors: Yu Wen Hsu, Tainan (TW); Chin Fu Kuo, Tainan (TW); Chao Ta Huang, Hsinchu (TW); Chun Kai Mao, Tainan (TW); Chin Hung Wang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/094,568

(22) Filed: Dec. 2, 2013

(65) Prior Publication Data
US 2014/0175572 A1    Jun. 26, 2014

(30) Foreign Application Priority Data

Dec. 20, 2012  (TW) ............................. 101148598 A
Mar. 28, 2013  (CN) ........................... 2013 1 0105428
Jun. 4, 2013   (TW) ............................. 102119719 A

(51) Int. Cl.
*A61B 19/00*    (2006.01)
*B81B 3/00*     (2006.01)
(Continued)

(52) U.S. Cl.
CPC .............. *B81B 3/0086* (2013.01); *G01L 9/0073* (2013.01); *G01P 15/0802* (2013.01);
(Continued)

(58) Field of Classification Search
CPC .................... B81B 3/0086; B81B 2201/0221; B81B 2201/0235; B81B 2201/0242; B81B 2201/0257; B81B 2201/0264; B81B 1/00; G01L 9/0072; G01L 15/00; G01P 15/0802; G01P 15/125; G01P 2015/0837; H01G 1/00; H01L 21/00; H01L 41/113; H01L 41/1132; H01L 41/1134; H01L 41/1136; H01L 2924/1461; A61B 2562/0247; A61B 2562/028; A61B 2562/0285
USPC ................................................... 257/414–419
See application file for complete search history.

(56) References Cited

U.S. PATENT DOCUMENTS 3,993,939 A   11/1976  Slavin et al.
4,064,550 A   12/1977  Dias et al.
(Continued)

FOREIGN PATENT DOCUMENTS

CN    101614604     1/2011
CN    102323449    11/2012
CN    102807189    12/2012

OTHER PUBLICATIONS

Meng Nie et al., Design of a Capacitive Pressure Sensor Based On Flip-Chip Packaging Technology, 11th International Conference on Electronic Packaging Technology & High Density Packaging, 2010, pp. 538-541.
(Continued)

*Primary Examiner* — Galina Yushina
(74) *Attorney, Agent, or Firm* — WPAT, P.C.; Anthony King

(57) ABSTRACT

A MEMS device with a first electrode, a second electrode and a third electrode is disclosed. These electrodes are disposed on a substrate in such a manner that (1) a pointing direction of the first electrode is in parallel with a normal direction of the substrate, (2) a pointing direction of the third electrode is perpendicular to the pointing direction of the first electrode, (3) the second electrode includes a sensing portion and a stationary portion, (4) the first electrode and the sensing portion are configured to define a sensing capacitor, and (5) the third electrode and the stationary portion are configured to define a reference capacitor. This arrangement facilitates the MEMS device such as a differential pressure sensor, differential barometer, differential microphone and decoupling capacitor to be miniaturized.

39 Claims, 33 Drawing Sheets

(51) Int. Cl.
*G01L 9/00* (2006.01)
*G01P 15/08* (2006.01)
*G01P 15/125* (2006.01)

(52) U.S. Cl.
CPC ......... *G01P15/125* (2013.01); *A61B 2562/028* (2013.01); *B81B 2201/0221* (2013.01); *B81B 2201/0235* (2013.01); *B81B 2201/0242* (2013.01); *B81B 2201/0257* (2013.01); *B81B 2201/0264* (2013.01); *G01P 2015/0837* (2013.01)

(56) References Cited

U.S. PATENT DOCUMENTS

| | | | |
|---|---|---|---|
| 4,422,125 | A | 12/1983 | Antonazzi et al. |
| 4,458,537 | A | 7/1984 | Bell et al. |
| 4,501,051 | A | 2/1985 | Bell et al. |
| 4,531,415 | A | 7/1985 | Orlowski et al. |
| 4,741,214 | A | 5/1988 | Vidmantas |
| 4,875,134 | A | 10/1989 | Kuisma |
| 4,972,717 | A | 11/1990 | Southworth et al. |
| 5,056,369 | A | 10/1991 | Tamai et al. |
| 5,259,247 | A | 11/1993 | Bantien |
| 5,332,469 | A | 7/1994 | Mastrangelo |
| 5,349,492 | A | 9/1994 | Kimura et al. |
| 5,369,544 | A | 11/1994 | Mastrangelo |
| 5,470,797 | A | 11/1995 | Mastrangelo |
| 5,510,276 | A | 4/1996 | Diem et al. |
| 5,925,824 | A | 7/1999 | Soma et al. |
| 6,051,853 | A | 4/2000 | Shimada et al. |
| 6,122,973 | A | 9/2000 | Nomura et al. |
| 6,236,096 | B1 * | 5/2001 | Chang et al. ................. 257/419 |
| 6,257,068 | B1 | 7/2001 | Briefer et al. |
| 6,311,563 | B1 | 11/2001 | Ishikura |
| 6,470,754 | B1 | 10/2002 | Gianchandani |
| 6,564,643 | B1 * | 5/2003 | Horie et al. ..................... 73/724 |
| 6,651,506 | B2 * | 11/2003 | Lee et al. ..................... 73/718 |
| 6,945,115 | B1 | 9/2005 | Wang |
| 7,082,024 | B2 | 7/2006 | Casset et al. |
| 7,135,749 | B2 | 11/2006 | Sakai et al. |
| 7,150,195 | B2 | 12/2006 | Jacobsen et al. |
| 7,200,908 | B2 | 4/2007 | Cassett et al. |
| 7,270,011 | B2 | 9/2007 | Vossenberg |
| 7,565,725 | B2 | 7/2009 | Bouche et al. |
| 7,841,239 | B2 | 11/2010 | Miyashita |
| 7,938,014 | B2 | 5/2011 | Meehan et al. |
| 2005/0200241 | A1 * | 9/2005 | Degertekin ................. 310/334 |
| 2006/0081043 | A1 * | 4/2006 | Silverbrook et al. ........... 73/146 |
| 2009/0031809 | A1 * | 2/2009 | Lin et al. ..................... 73/514.32 |
| 2011/0126632 | A1 * | 6/2011 | McNeil et al. ................. 73/718 |
| 2013/0118265 | A1 * | 5/2013 | Besling et al. ................. 73/724 |

OTHER PUBLICATIONS

Y. Zhang et al., A High-Sensitive Ultra-Thin MEMS Capacitive Pressure Sensor, Transducers, Beijing, China, Jun. 5-9, 2011, pp. 112-115.

H. Berney et al., Determination of the effect of processing steps on the CMOS compatibility of a surface micromachined pressure sensor, J. Micromech. Microeng., 2001, pp. 402-408, vol. 11.

Carlos H. Mastrogelo et al., Surface-Micromachined Capacitive Differential Pressure Sensor with Lithographically Defined Silicon Diaphragm, Journal of Microelectromechanical Systems, June 1996, pp. 98-105, vol. 5, No. 2.

K. Knese et al., Novel Technology for Capacitive Pressure Sensor with Monocrystalline Silicon Membranes, IEEE, 2009, pp. 697-700.

Chinese Office Action issued on Aug. 20, 2015 for counterpart Chinese application No. 201310105428.8.

* cited by examiner

MEMS DEVICE WITH MULTIPLE ELECTRODES AND FABRICATING METHOD THEREOF

The present application claims priority from Taiwanese application Ser. No. 101148598, filed on Dec. 20, 2012, and Ser. No. 102119719, filed on Jun. 4, 2013, of the same title and inventorship herewith and from Chinese application Ser. No. 201310105428.8, filed on Mar. 28, 2013, of the same title and inventorship herewith.

1. TECHNICAL FIELD

The present disclosure relates to a MEMS device and a fabricating method thereof, and more particularly, to a multiple-electrode MEMS device having a first capacitor and a second capacitor, and a fabricating method thereof.

2. BACKGROUND

Pressure sensors may be embedded into various mobile devices such as cell-phones, laptops, tablet computers, and vehicle navigation systems. Mobile devices with the pressure sensors are capable of performing 3-dimension navigation. In the future, applications of 3-dimension navigation may include indoor navigation, and outdoor navigation for tunnel, bridge and overpass. Thus, the navigation system requires an update from Global Positioning System (GPS) with 9-axis inertial sensors (including an accelerometer, a gyroscope and a magnetometer) to GPS with 10-axis inertial navigator (including an accelerometer, a gyroscope, a magnetometer and an air pressure sensor (also called a "barometer").

Generally, the higher the altitude, the lower the air pressure. The barometer (one kind of pressure sensor) is used to detect the change in air pressure so as to evaluate the change in altitude. A conventional air pressure sensor 1 shown in FIG. 1 includes a substrate 2, a stationary electrode 3 and a cover 4. The cover 4 is disposed on the substrate 2 and shelters the stationary electrode 3. In addition, the cover 4 includes a diaphragm 4-1. A hermetic space 5 is defined between the diaphragm 4-1 and the stationary electrode 3.

The conventional air-pressure sensor 1 includes two types of sensors. One type of the air-pressure sensors is utilized to detect absolute pressure while the other type of the air-pressure sensors is used to measure relative pressure. For detecting the absolute pressure, the hermetic space 5 of the former sensor is vacuum. When such a sensor is placed in an environment where an external air pressure P exists relative to the cover 4, the diaphragm 4-1 will deform. The deformation will change the capacitance between the diaphragm 4-1 and the stationary electrode 3 due to a change in the distance therebetween. In accordance with the change in capacitance, a processor may calculate an air-pressure value. Thus, the air-pressure value is an absolute pressure value of the external air-pressure P.

Regarding the sensor for measuring relative pressure, there is a gas-pressure $P_1$ in the hermetic space 5. As shown in FIG. 2, in a certain altitude, when the external air-pressure maintains at $P_2$, the diaphragm 4-2 will produce deformation $d_1$. The deformation will change the capacitance between the diaphragm 4-2 and the stationary electrode 3-1 due to a change in the distance therebetween. In accordance with the change in capacitance, a processor may calculate an air-pressure value. Thus, the air-pressure value is a relative pressure value between the gas-pressure $P_1$ and the external air-pressure. Either the sensors for absolute pressure or the sensors for relative pressure are capable of calculating the change of altitude according to the above-mentioned pressure values, but in those sensors only a single capacitor is provided, which is liable to error in pressure measurement due to undesirable noise of the single capacitor.

In order to improve the conventional pressure sensors, as shown in FIG. 3, a differential pressure sensor 6 is designed with a sensing capacitor 7 including a movable electrode 7-1 and a stationary electrode 7-2, and with a reference capacitor 8 including two stationary electrodes 8-1 and 8-2. The differential pressure sensor 6 is capable of calculating the differential capacitance between the sensing capacitor 7 and the reference capacitor 8 so as to reduce noise.

FIG. 4 is a top view of the differential pressure sensor 6. As shown in FIG. 4, a reference capacitor 8 of the differential pressure sensor 6 increases the entire area of the differential pressure sensor 6. Thus, it is difficult for the differential pressure sensor 6 to use in a mobile device. FIG. 3 illustrates a cross-sectional view of the differential pressure sensor 6, taken from the line 1-1 in FIG. 4.

A differential pressure sensor 9 shown in FIG. 5 includes a first electrode 9-1, a second electrode 9-2 and a third electrode 9-3. The first electrode 9-1 and the third electrode 9-3 form a reference capacitor while the first electrode 9-1 and the second electrode 9-2 form a sensing capacitor. When an external pressure causes the first electrode 9-1 to deform, the distance between the first electrode 9-1 and the third electrode 9-3 is changed and the capacitance of a stationary electrode is affected. Consequently, an error results in the calculation based on the capacitance difference between the sensing capacitor and the reference capacitor.

SUMMARY

The present disclosure provides a MEMS device with multiple electrodes. The MEMS device includes a sensing capacitor and a reference capacitor. The second electrode of the MEMS device includes two portions. One portion is sensing portion, which is configured for forming the sensing capacitor, while the other portion is the stationary portion, which is configured for forming the reference capacitor. In other words, one electrode of the sensing capacitor and one electrode of the reference capacitor both are located at the second electrode having the same electric potential.

The present disclosure provides a MEMS device having multiple vertical electrodes. The MEMS device includes a substrate, a first electrode, a second electrode and a third electrode.

The first electrode, the second electrode and the third electrode are disposed on the substrate. The second electrode includes a sensing portion and a stationary portion. A variable capacitor may be defined between the sensing portion of the second electrode and the first electrode. The variable capacitor may be also called a sensing capacitor in the present disclosure. A stationary capacitor may be defined between the stationary portion of the second electrode and the third electrode. The stationary capacitor may be also called a reference capacitor in the present disclosure.

When the second electrode deforms due to the external pressure such as air pressure, the stationary portion and the third electrode are spaced apart by a predetermined constant distance. In other words, when sensing portion of the second electrode deforms, the distance between the stationary portion and the third electrode is constant as expected.

The present disclosure also provides another MEMS device with multiple electrodes including a substrate, a first electrode, a second electrode and a third electrode.

The first electrode and the third electrode are disposed on the substrate. The first electrode and the second electrode are configured to form a sensing capacitor. The third electrode is configured to form a stationary capacitor (also called the reference capacitor). The third electrode does not electrically connect with the second electrode or the third electrode disconnects from the first electrode.

The included angle between the pointing direction of the first electrode and the pointing direction of the second electrode is substantially 90°.

Moreover, the present disclosure also provides a MEMS device which includes a substrate, a first electrode, a second electrode and a third electrode.

The first electrode is disposed on the substrate. The pointing direction of the first electrode is in parallel with the normal direction of the substrate. The second electrode is disposed on the substrate and the second electrode includes a sensing portion and a stationary portion. The sensing portion faces the first electrode.

The third electrode is disposed on the substrate. The stationary portion faces the third electrode while the pointing direction of the third electrode is perpendicular to the pointing direction of the first electrode. The sensing portion faces the first electrode. The stationary portion faces the third electrode. When the sensing portion deforms, the stationary portion and the third electrodes are spaced apart by a predetermined constant distance.

The present disclosure also provide a fabricating method of a MEMS device. The fabricating method includes the following steps.

Silicon On Insulator (SOI) wafer is provided. The SOI wafer includes a device layer, an electrical insulation layer and a handle layer. The electrical insulation layer is disposed between the device layer and the handle layer.

The device layer is etched to form a recession and a plurality of slots exposing the electrical insulation layer. The slots and the recession define a second electrode and a third electrode in the device layer. In addition, the second electrode includes a sensing portion and a stationary portion.

The stationary portion is etched to form a conductive post and a through hole exposing the electrical insulation layer. A conductive post is disposed inside the through hole while the conductive post is electrically insulated from the stationary portion.

A substrate wafer is provided and then a first electrode is disposed on the substrate wafer.

The substrate wafer and the SOI wafer are bonded through wafer-to-wafer bonding process. The second electrode and the third electrode are connected to a top surface of the substrate wafer. The sensing portion faces the first electrode. The stationary portion faces the third electrode. The pointing direction of the third electrode is perpendicular to the pointing direction of the first electrode.

Finally, the handle layer is removed.

Another function of the present disclosure will be described at following paragraphs. Certain functions can be realized in present section, while the other functions can be realized in detailed description. In addition, the indicated components and the assembly can be explained and achieved by detail of the present disclosure. Notably, the previous explanation and the following description are demonstrated instead of limiting the scope of the present disclosure.

The foregoing has outlined rather broadly the features and technical benefits of the disclosure in order that the detailed description of the disclosure that follows may be better understood. Additional features and benefits of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes of the disclosure. It should also be realized by those skilled in the art that such equivalent constructions do not depart from the spirit and scope of the disclosure as set forth in the appended claims.

BRIEF DESCRIPTION OF THE DRAWINGS

The accompanying drawings, which are incorporated in and constitute a part of this specification, illustrate embodiments of the disclosure and, together with the description, serve to explain the principles of the invention.

The foregoing summary, as well as the following detailed description of the invention, will be better understood when read in conjunction with the appended drawings. For the purpose of illustrating the invention, there are shown in the drawings examples which are presently preferred. It should be understood, however, that the invention is not limited to the precise arrangements and instrumentalities shown.

Figure 1:
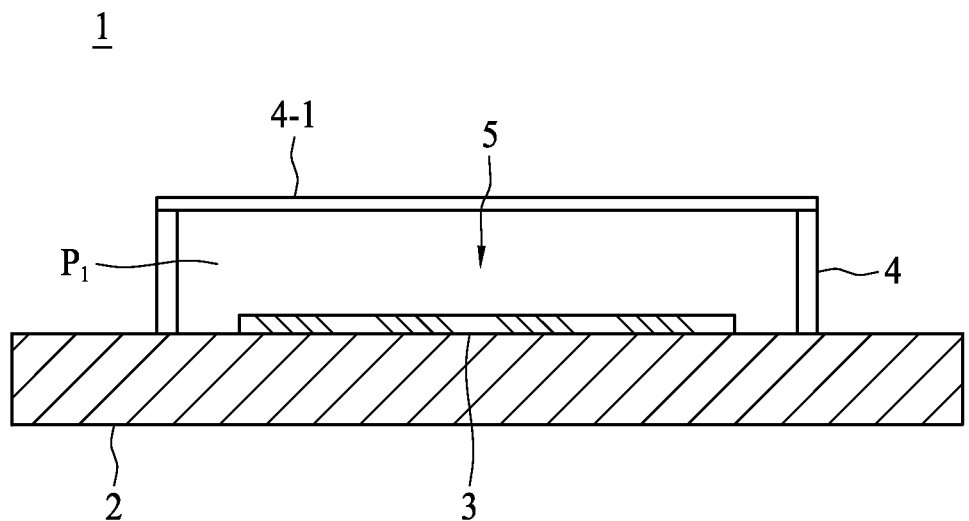
Figure 2:
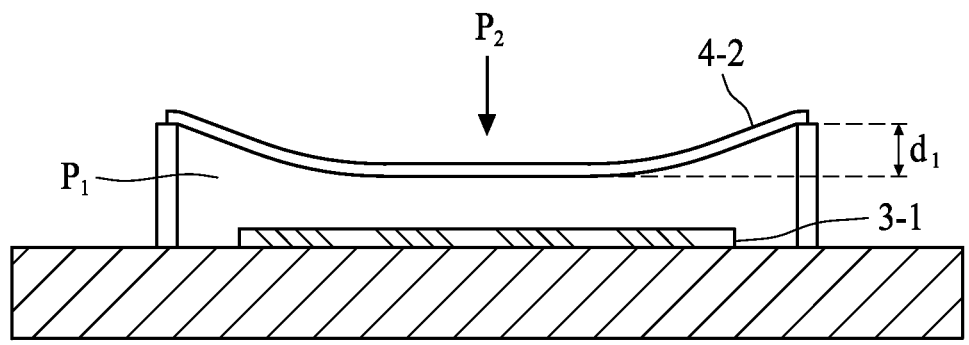
Figure 3:
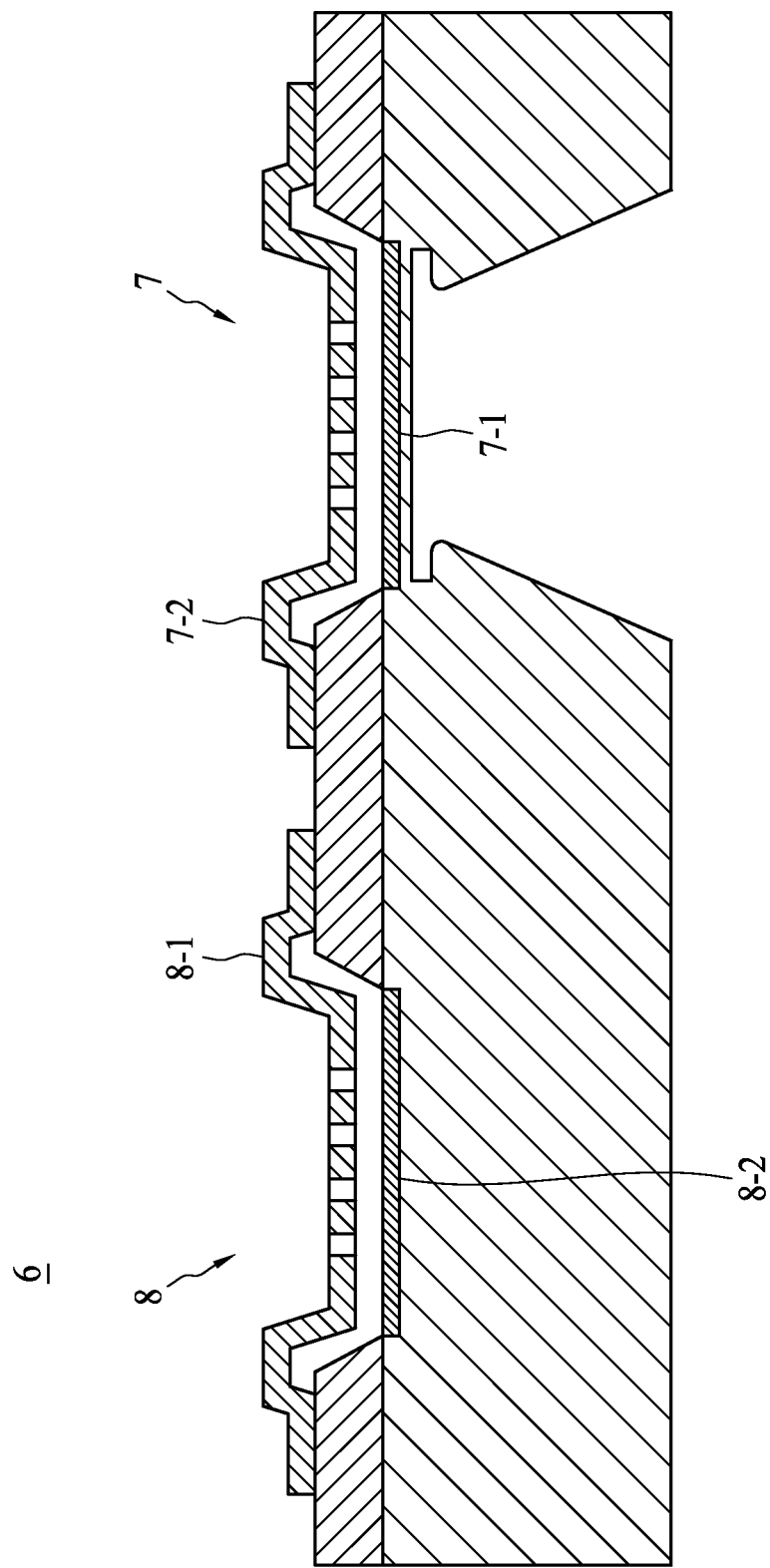
Figure 4:
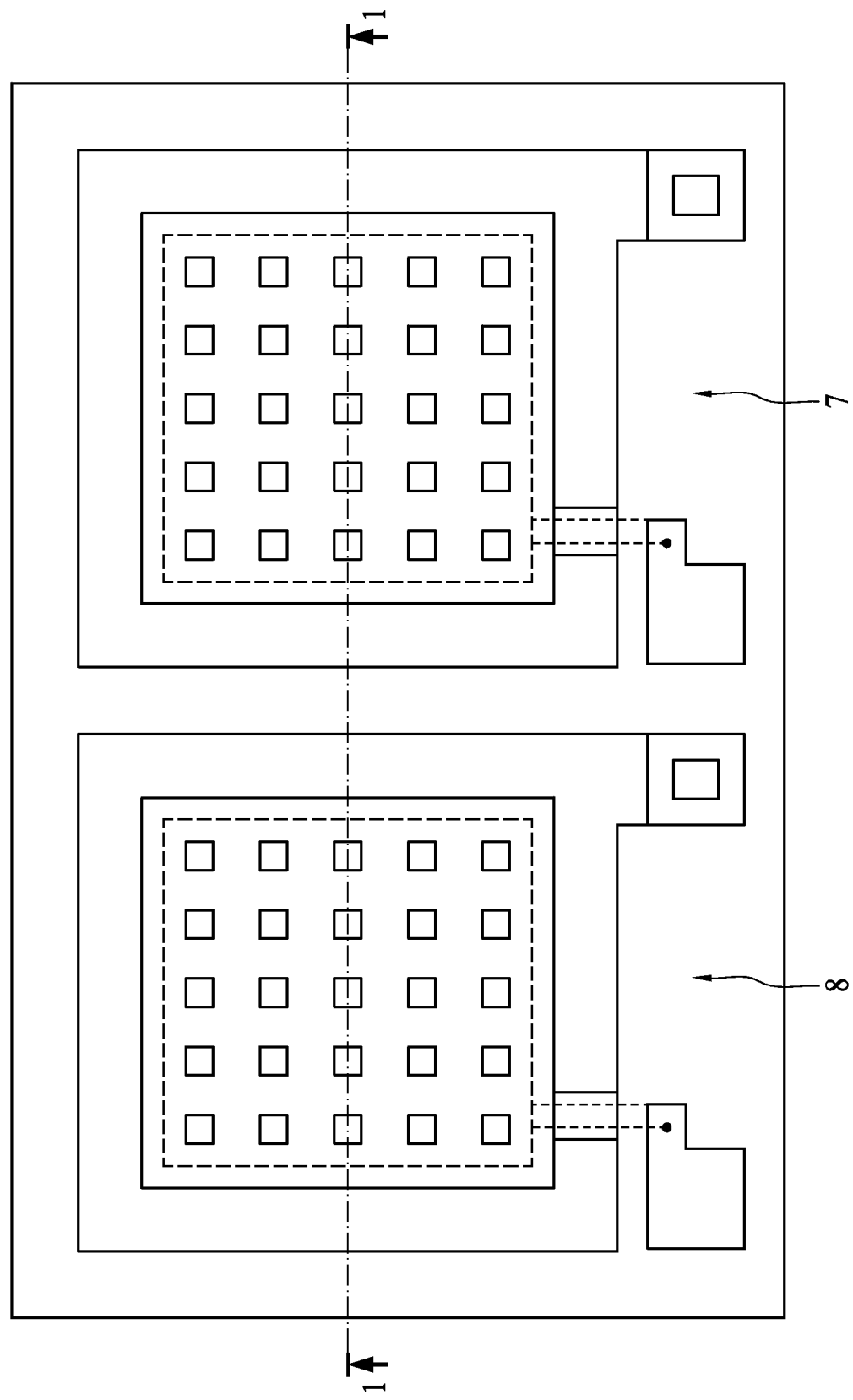
Figure 5:
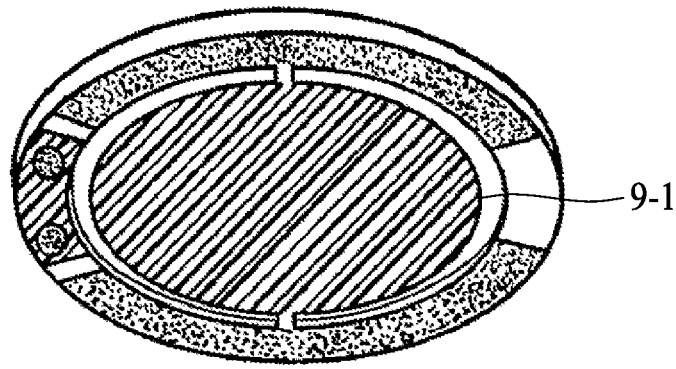
Figure 5:
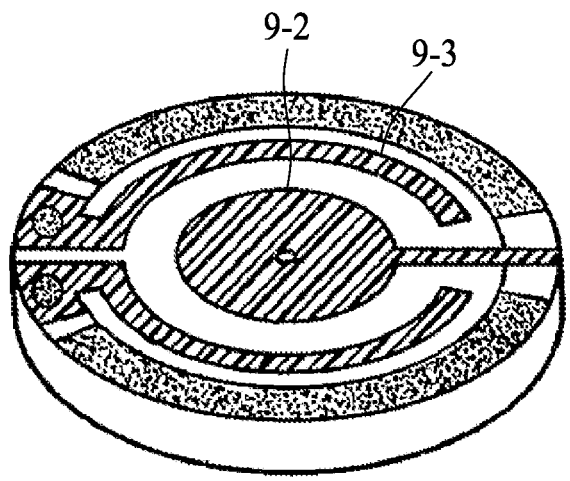
Figure 5:
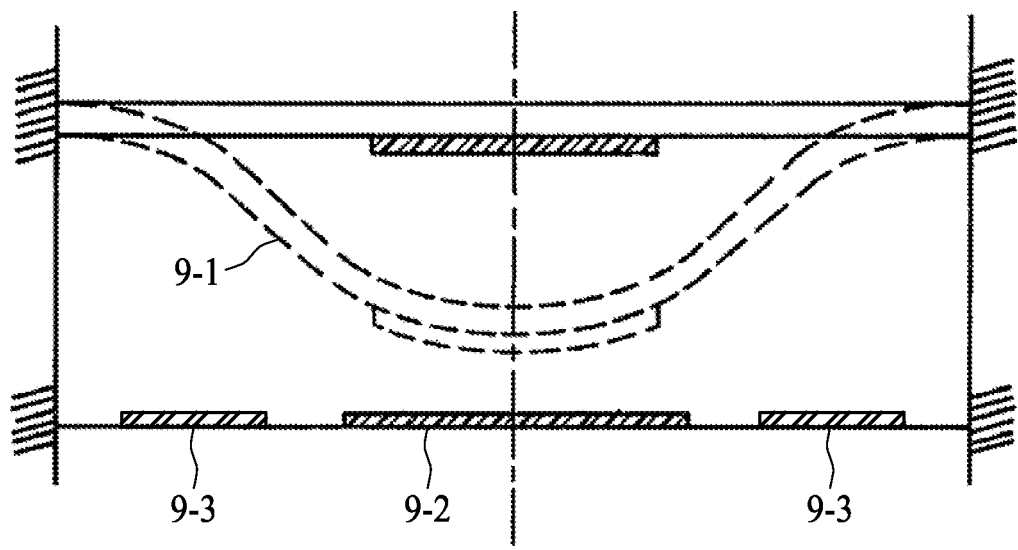
Figure 6:
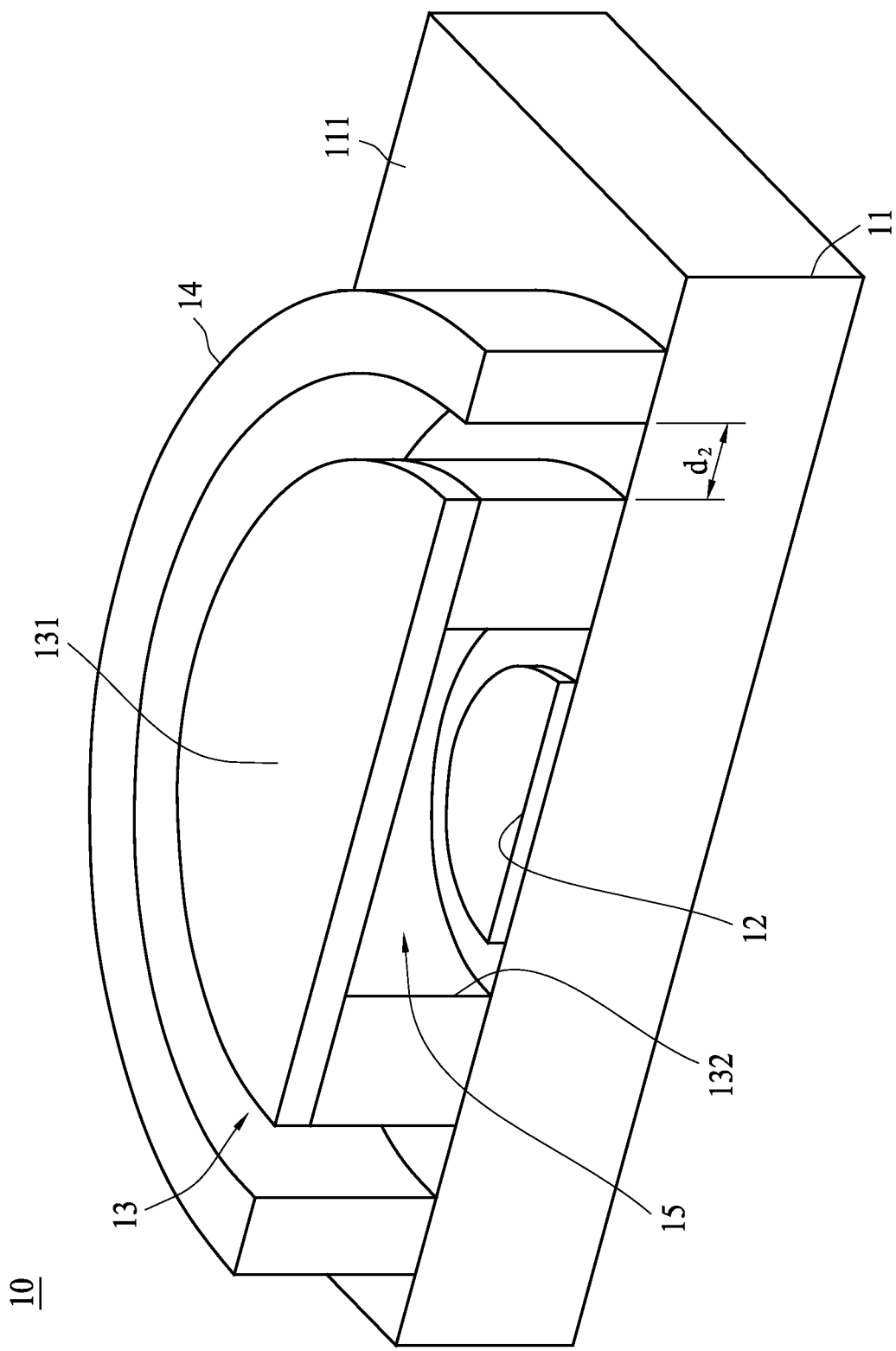
Figure 7:
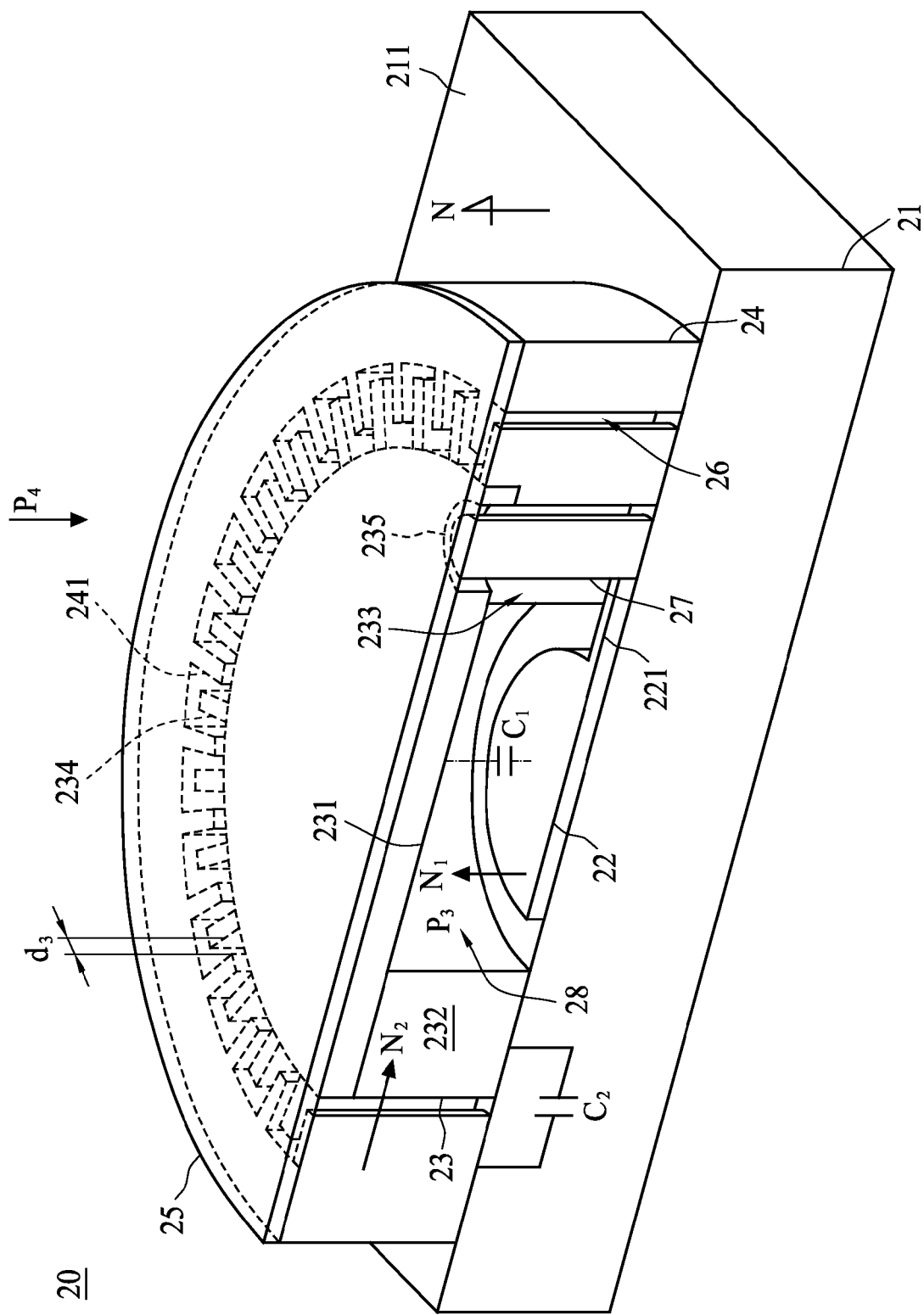
Figure 8:
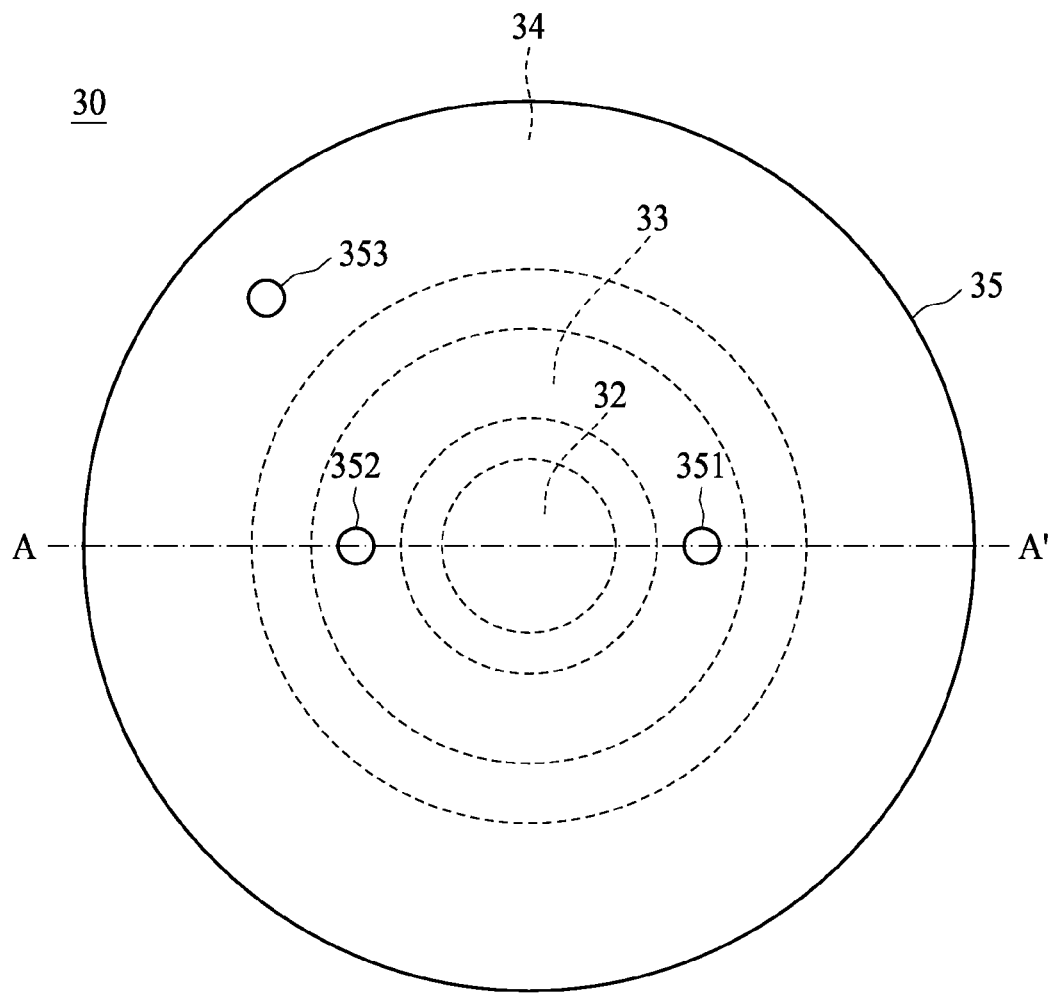
Figure 9:
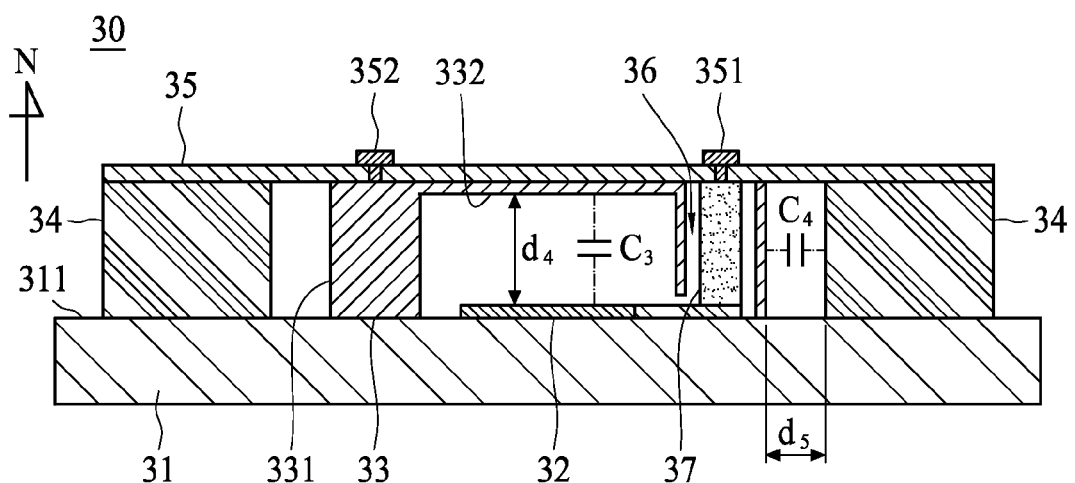
Figure 10:
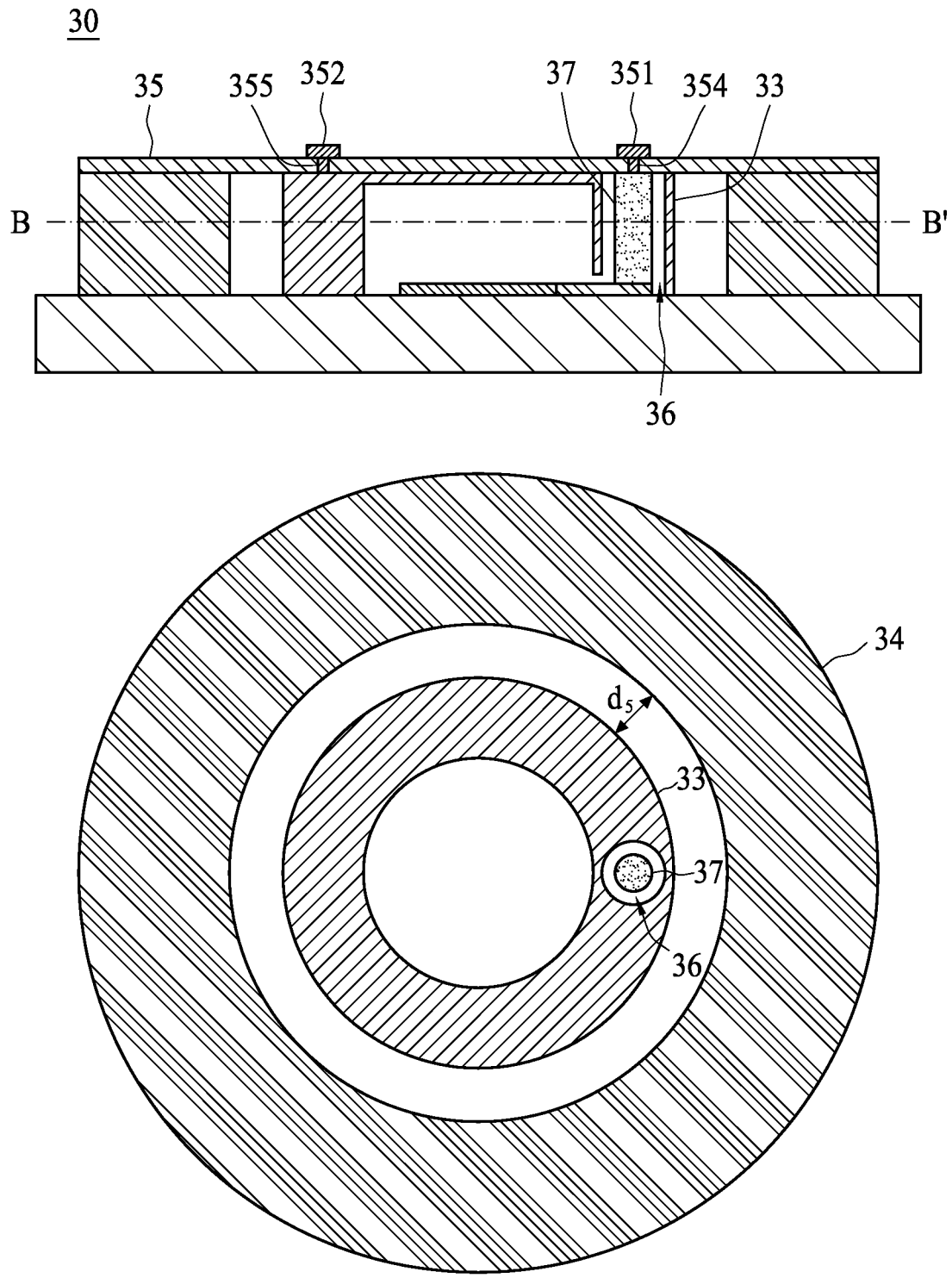
Figure 11:
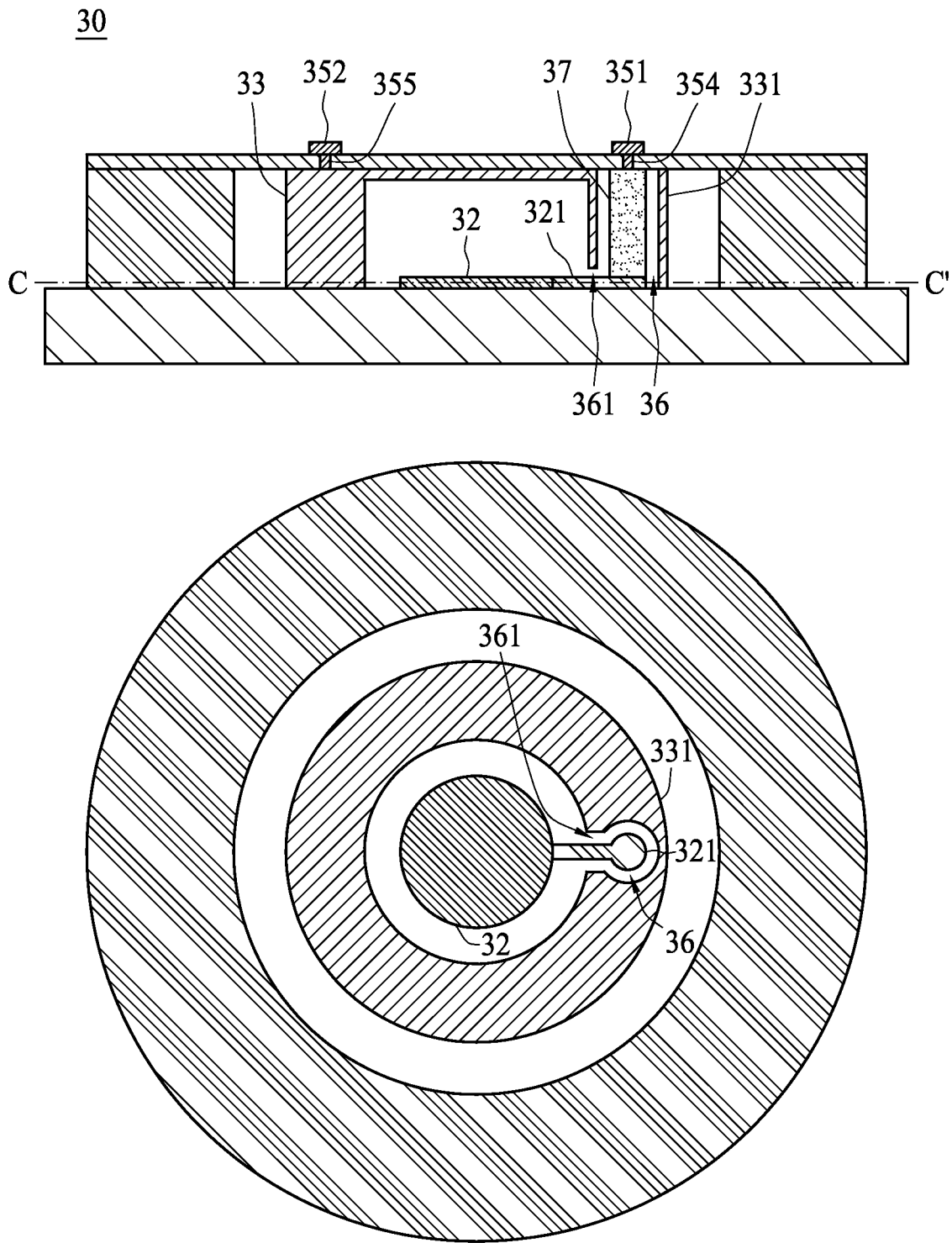
Figure 12:
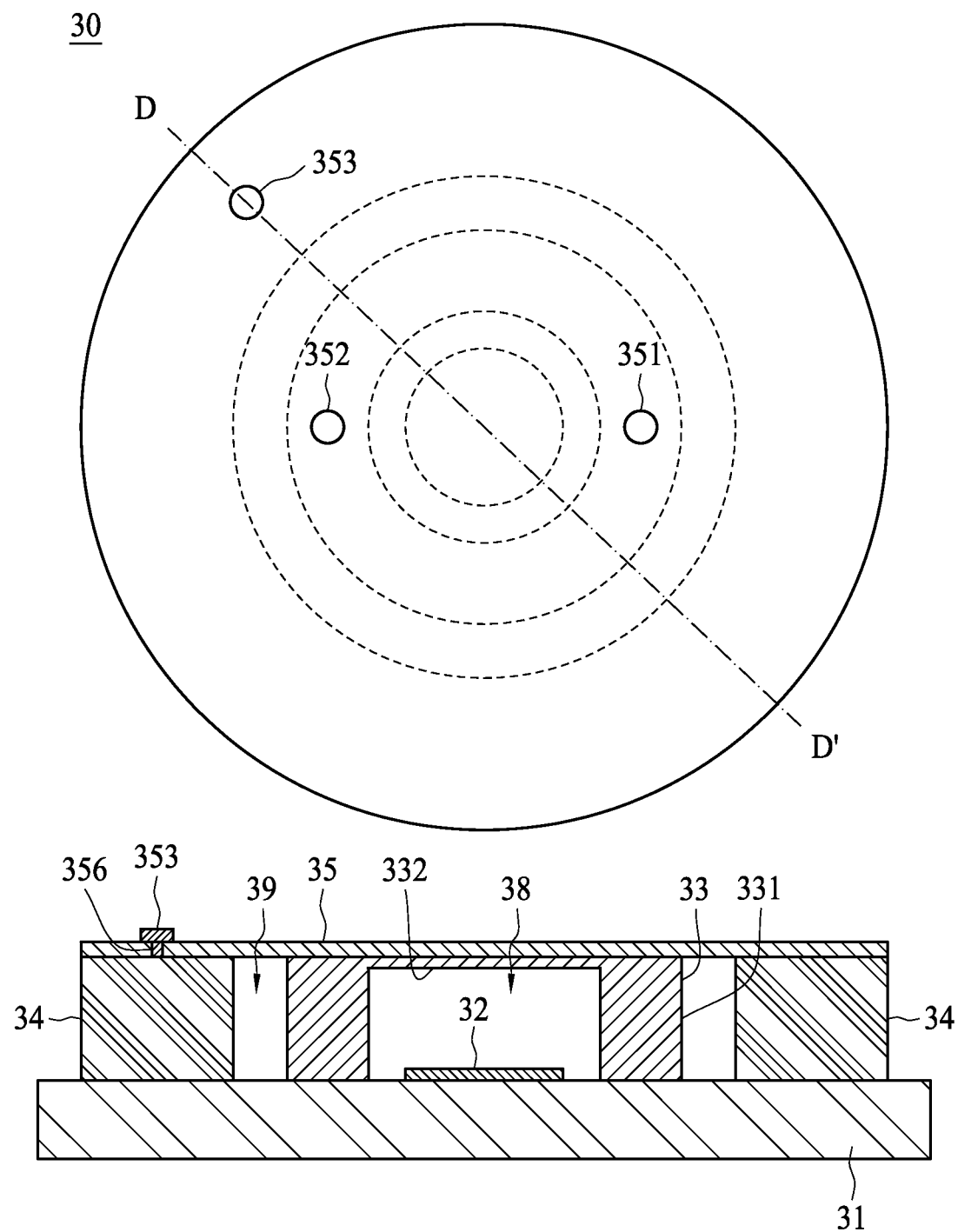
Figure 13:
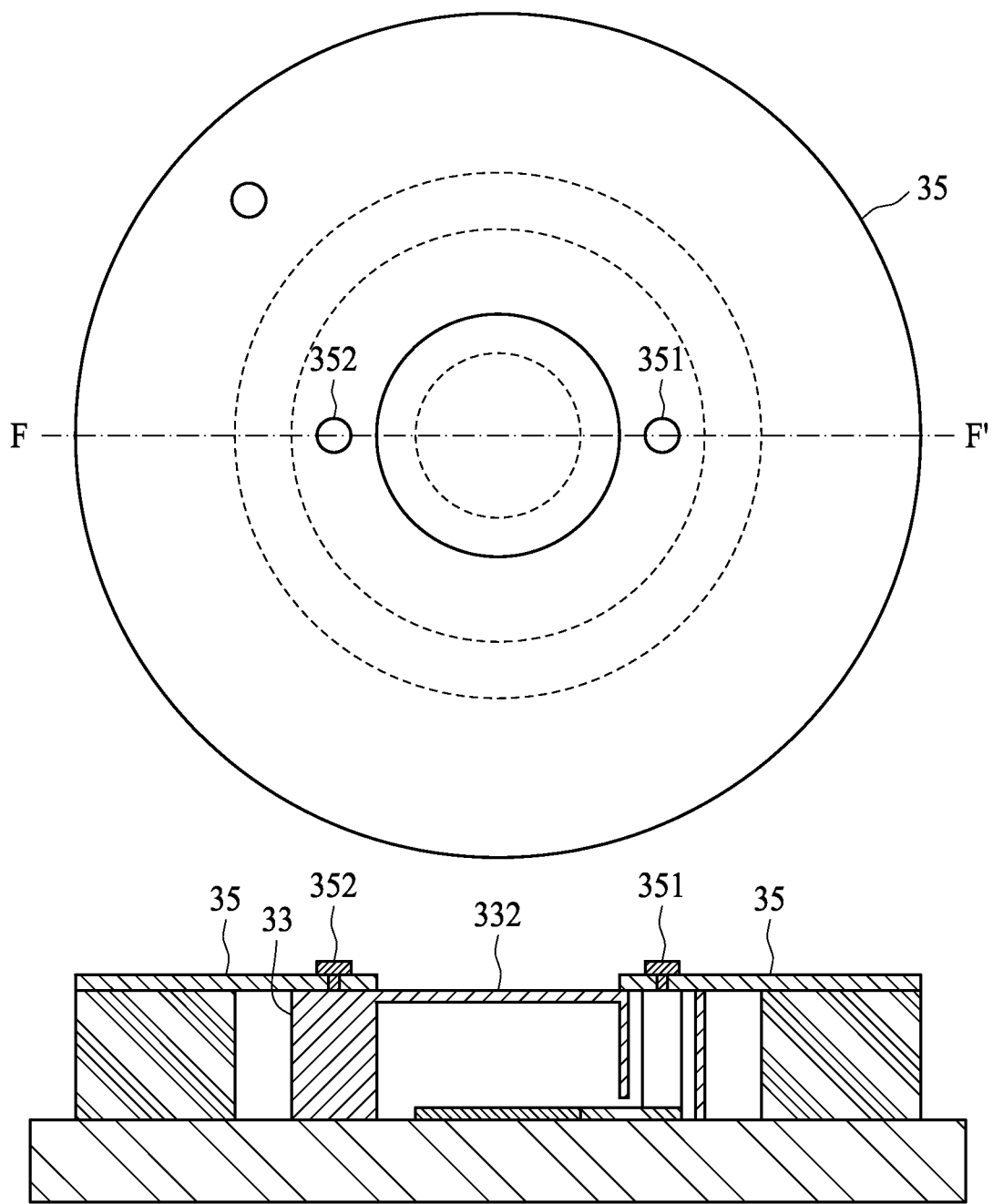
Figure 14:
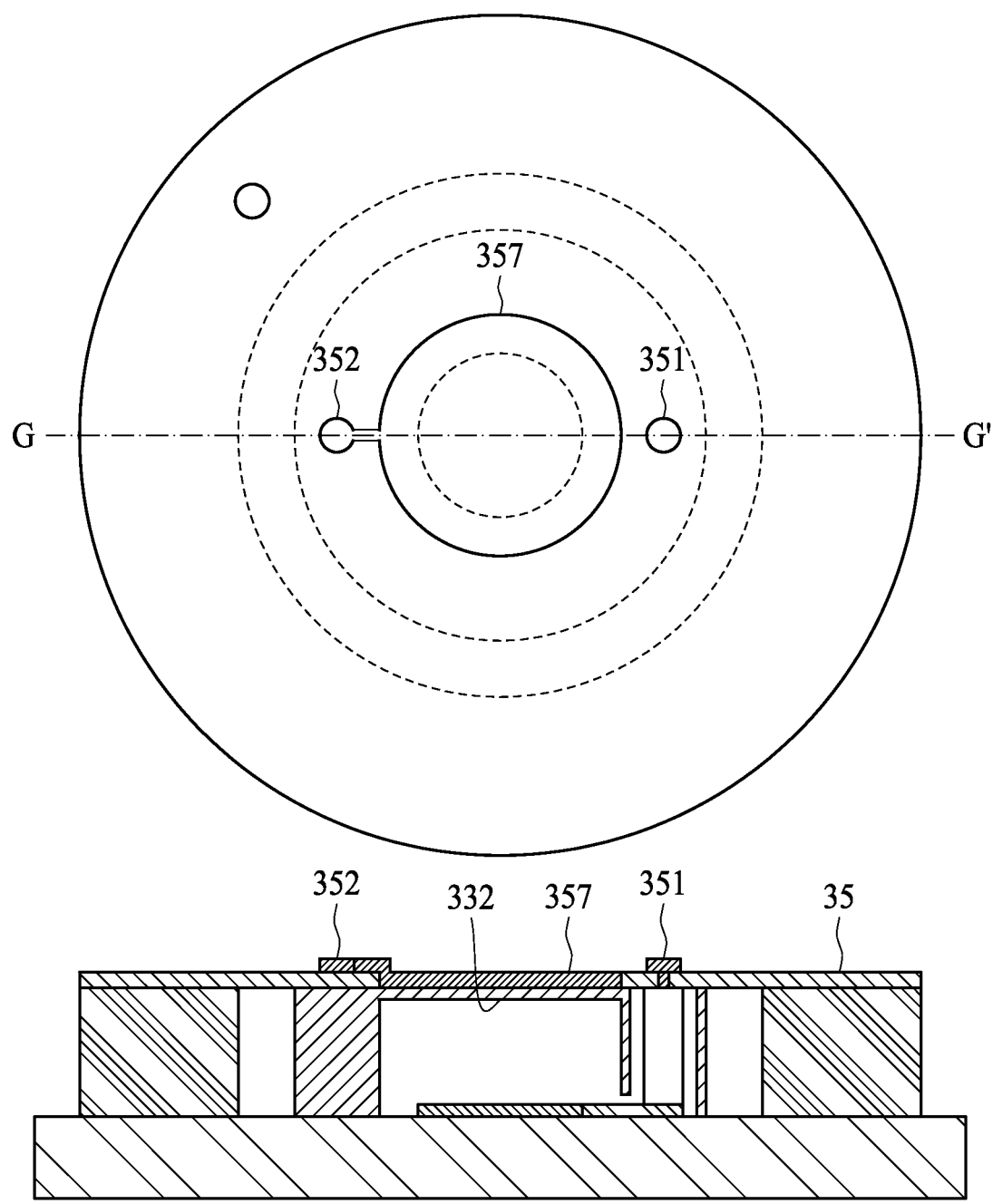
Figure 15:
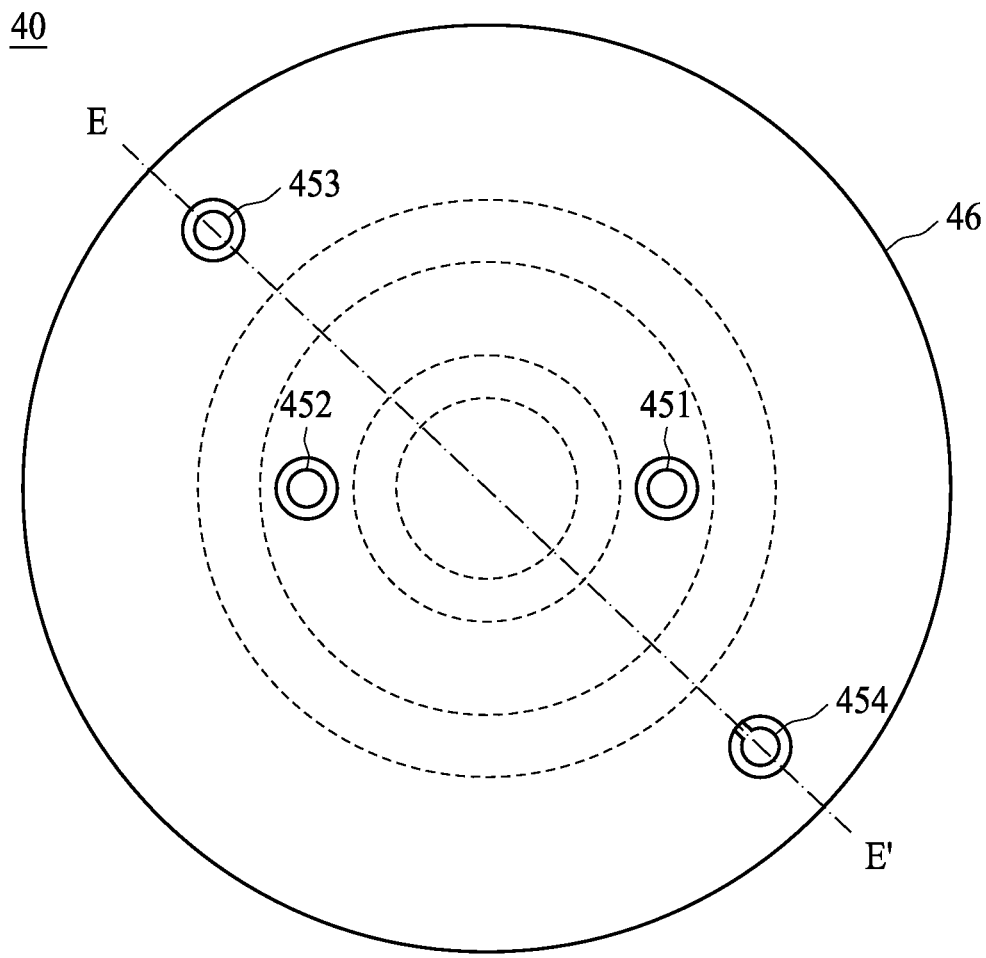
Figure 16:
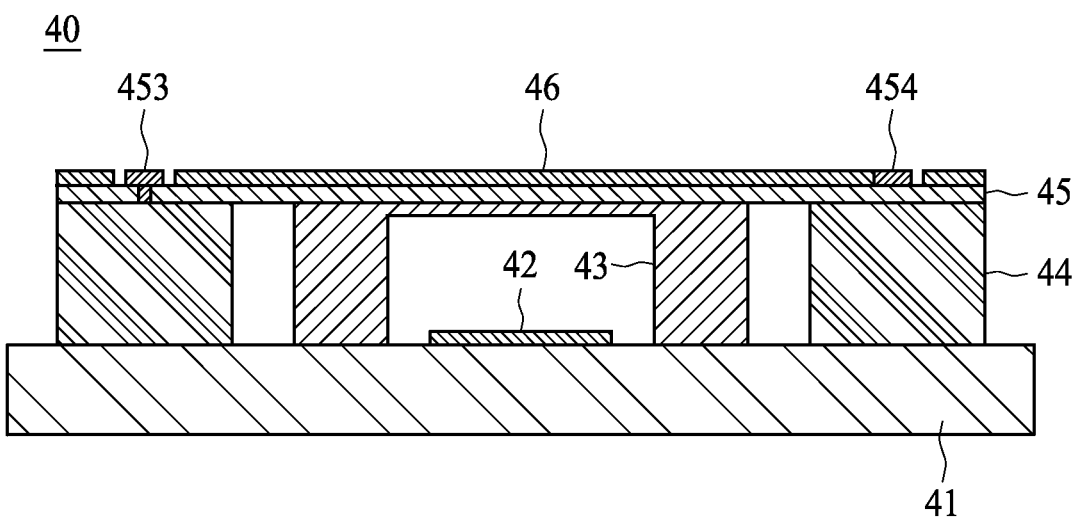
Figure 17:
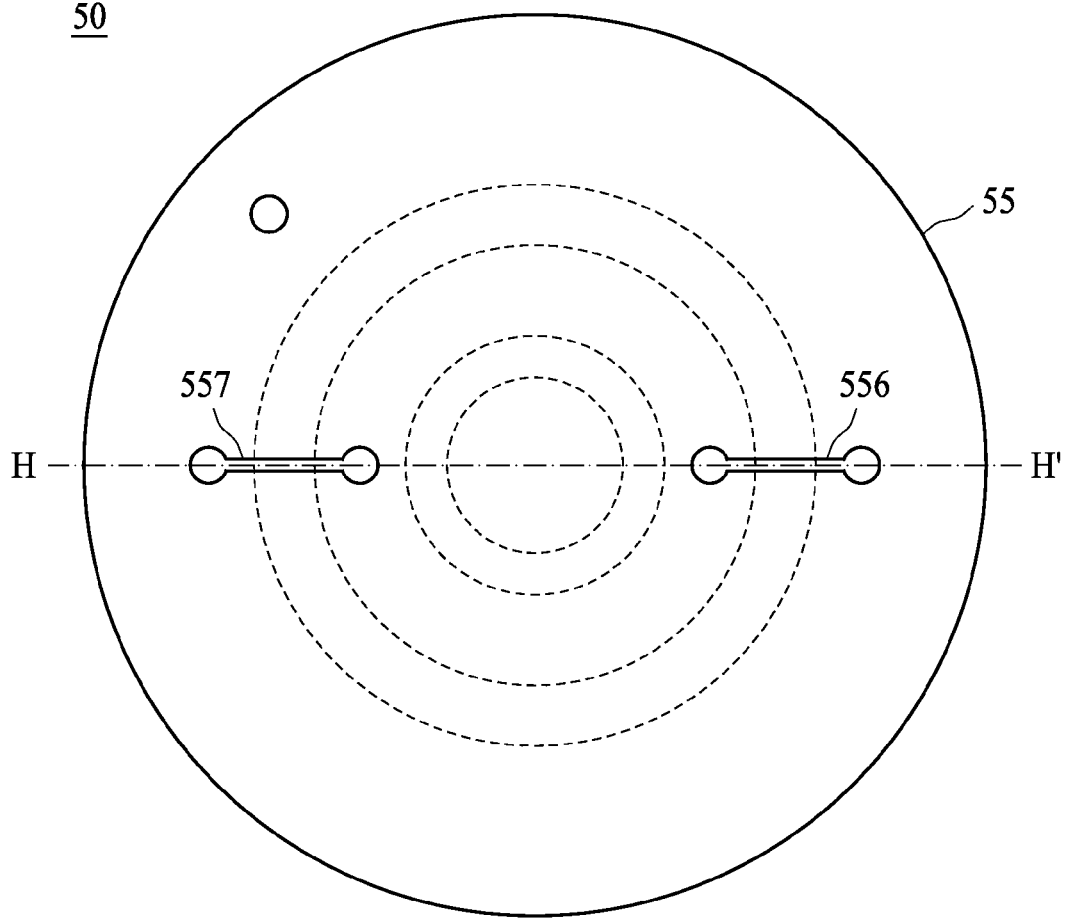
Figure 18:
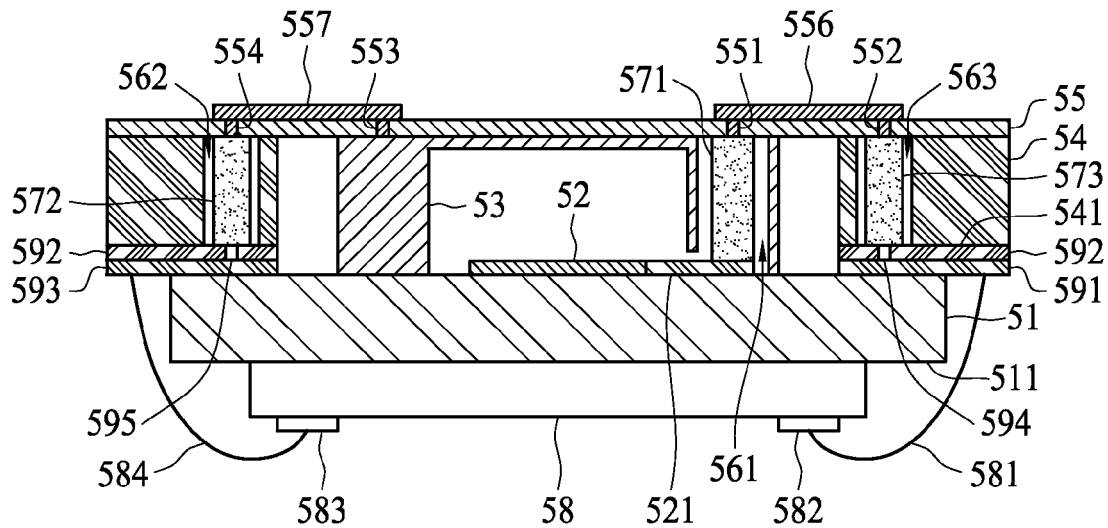
Figure 19:
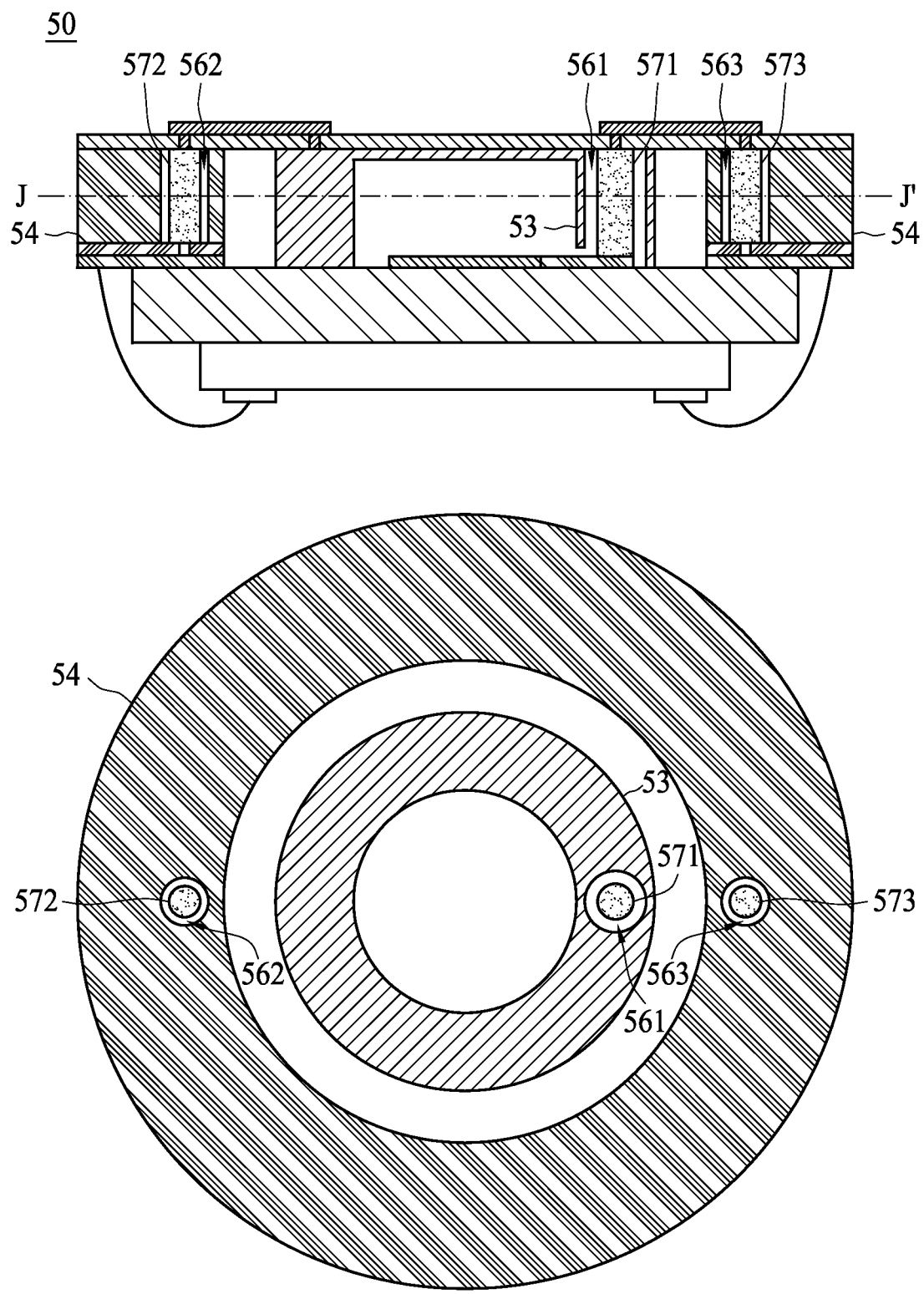
Figure 20:
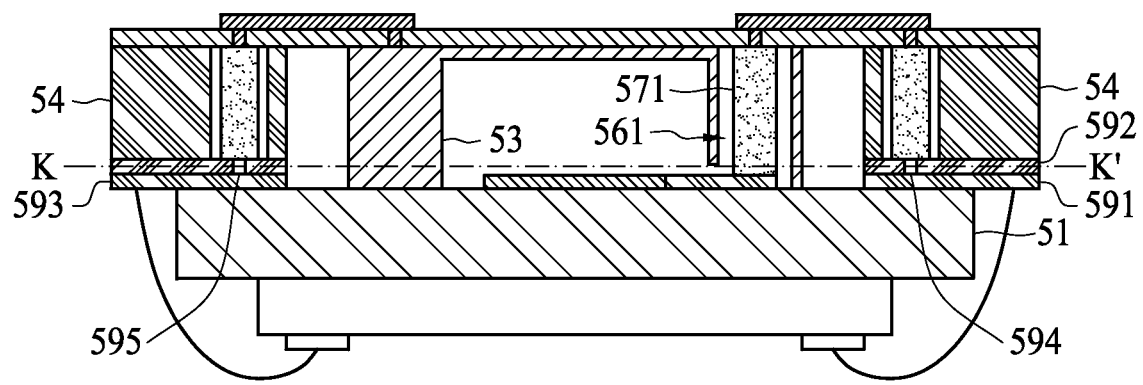
Figure 20:
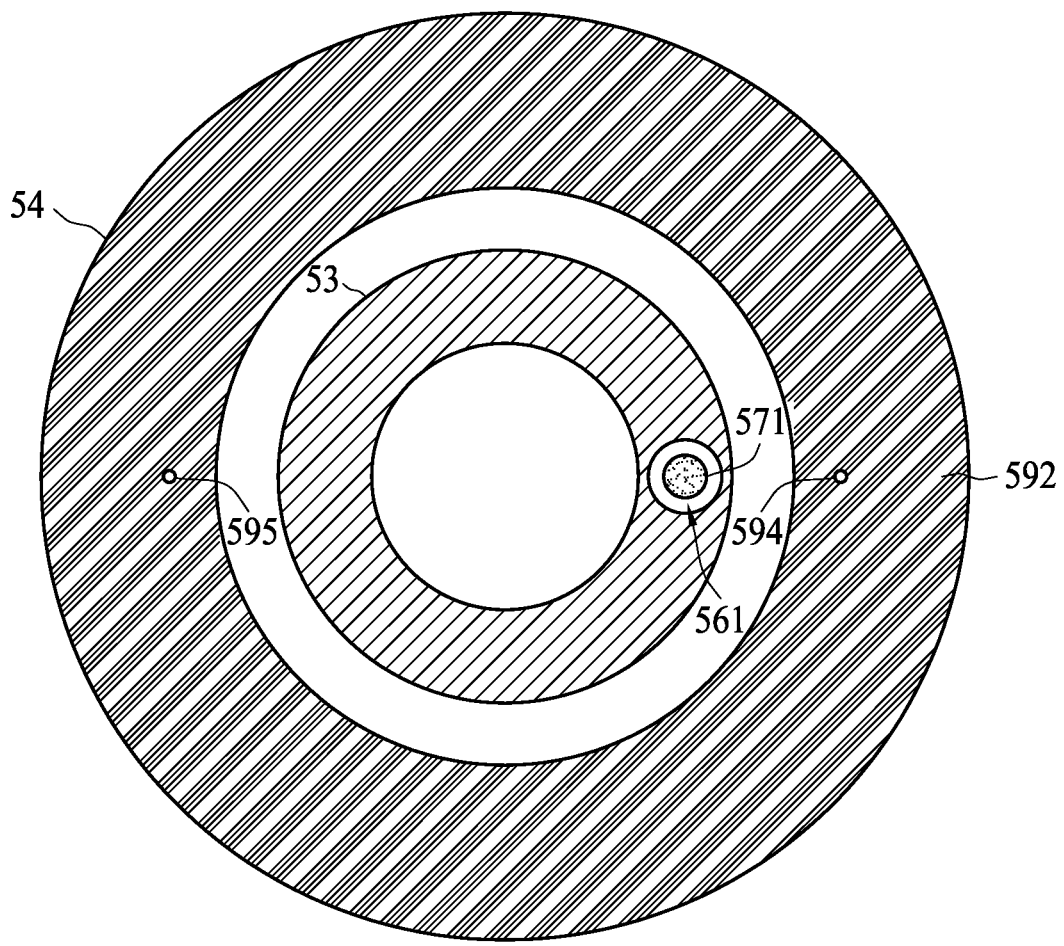
Figure 21:
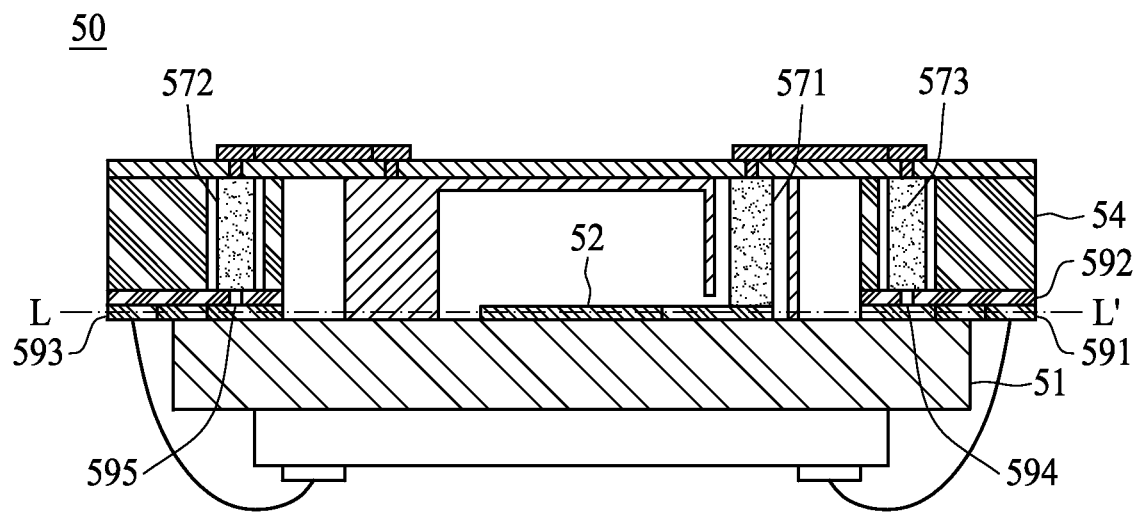
Figure 21:
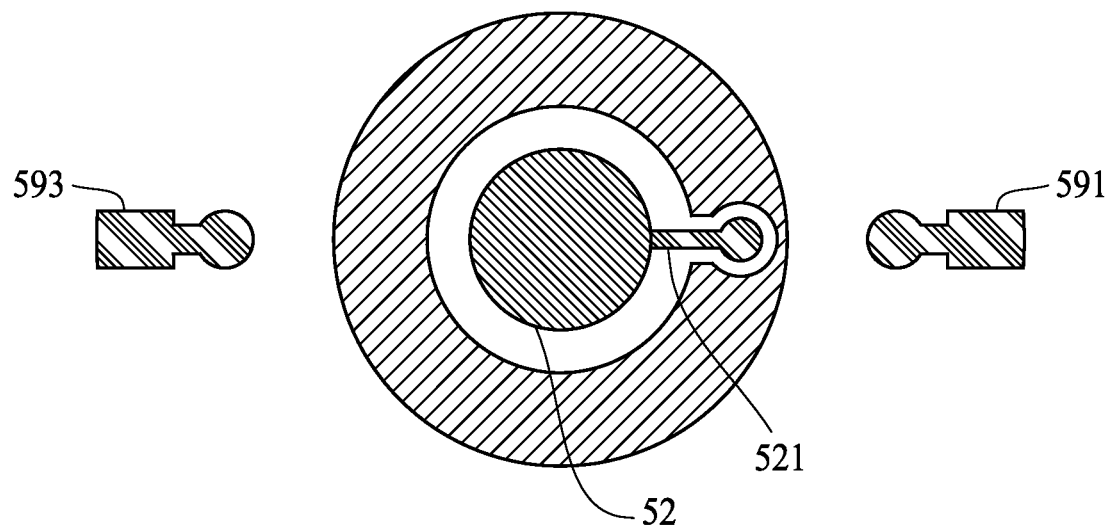
Figure 22:
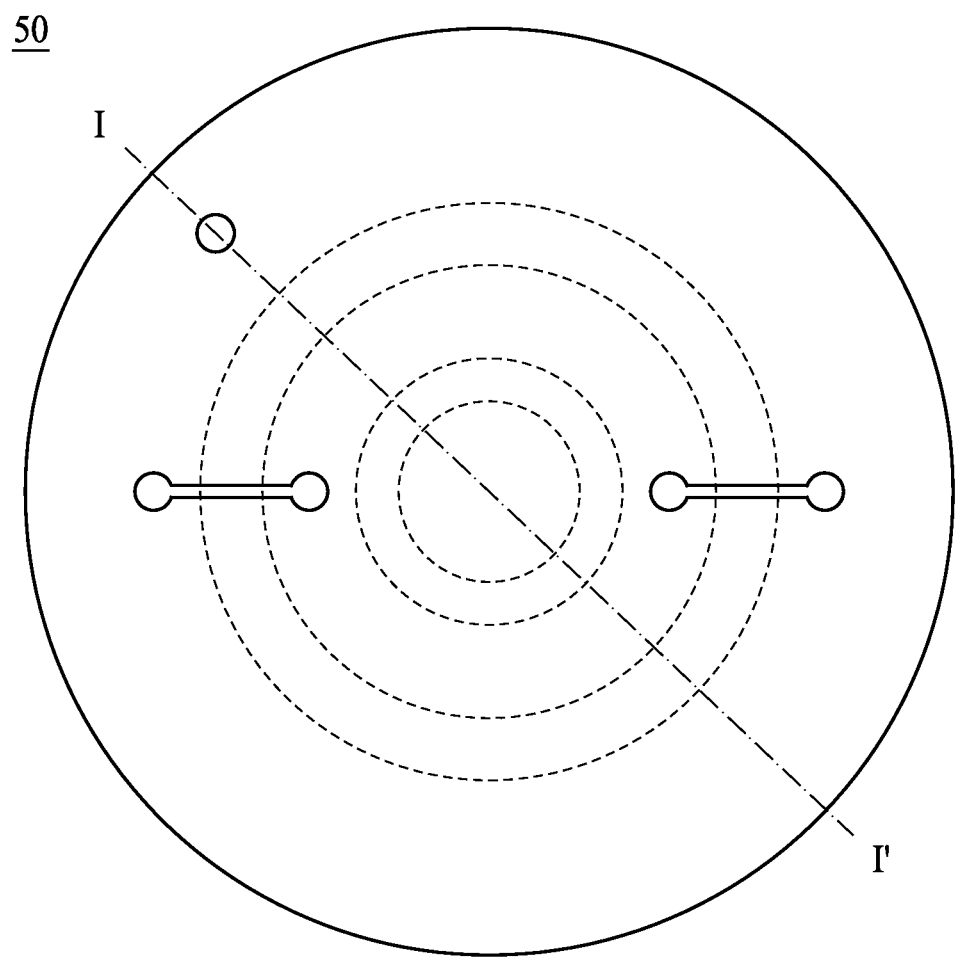
Figure 22:
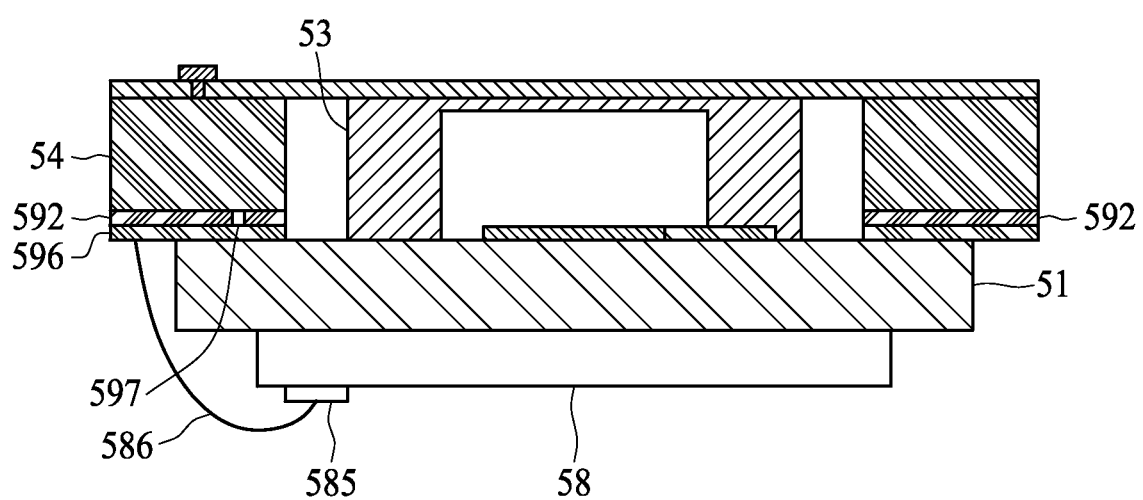
Figure 23:
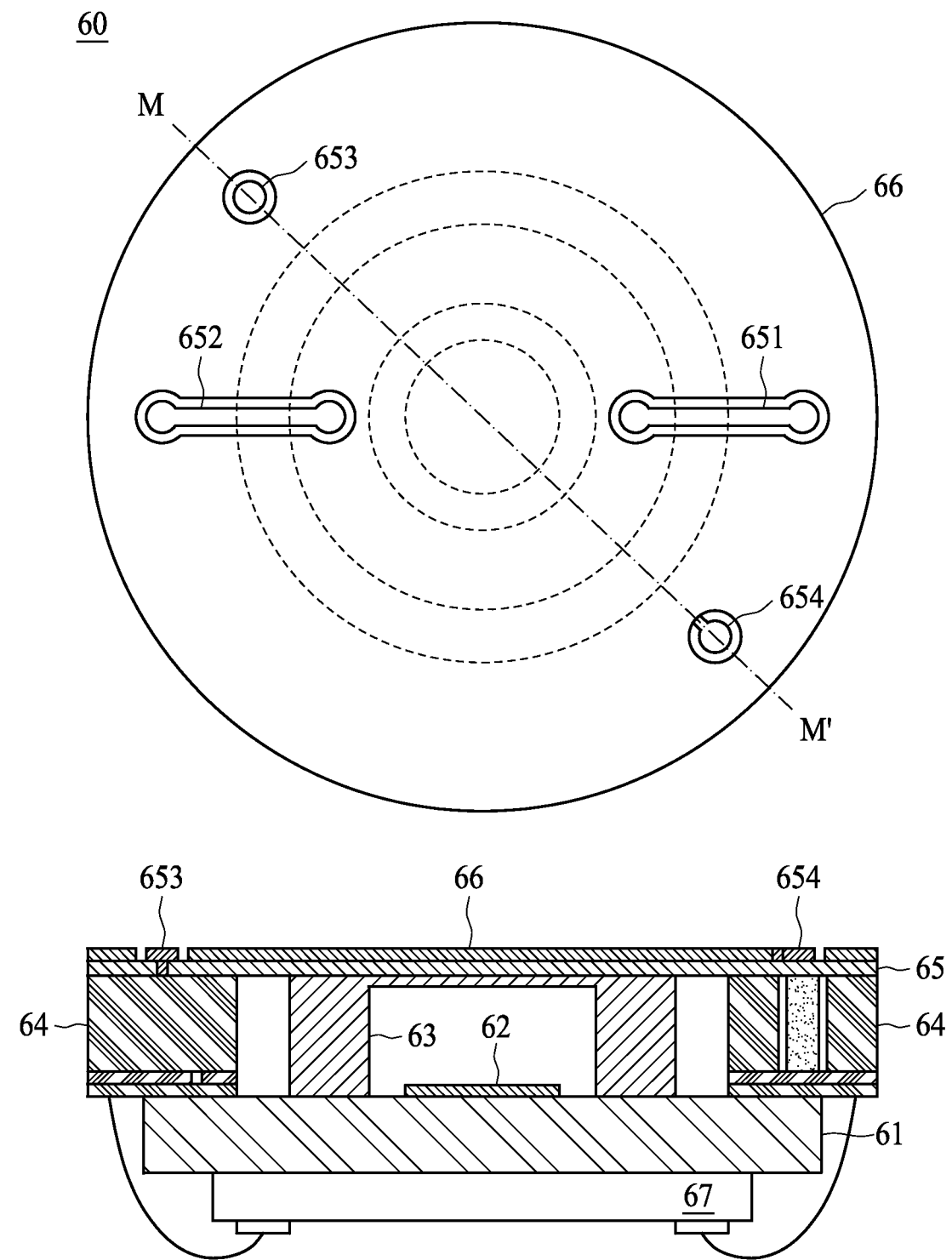
Figure 24:
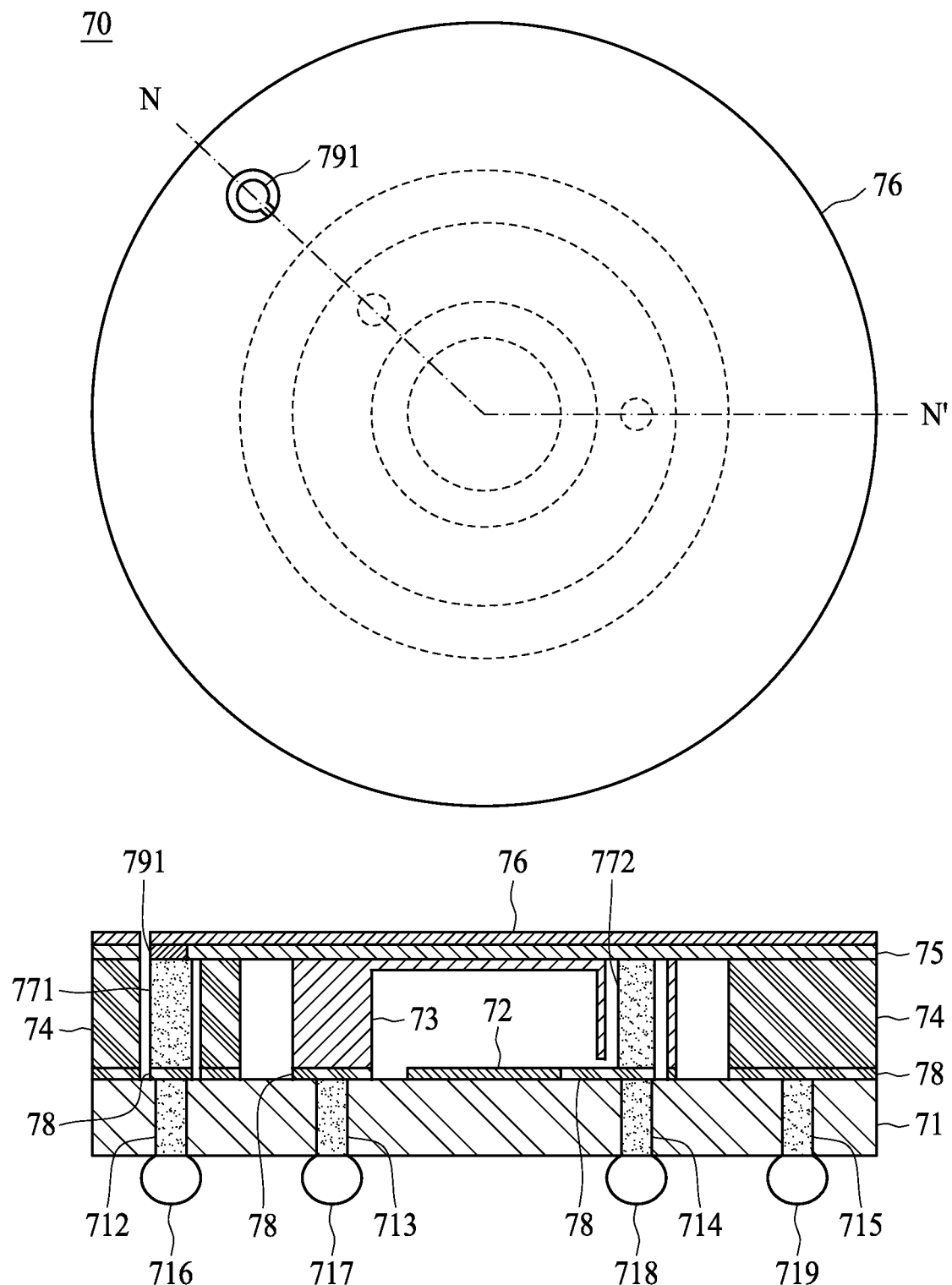
Figure 25:
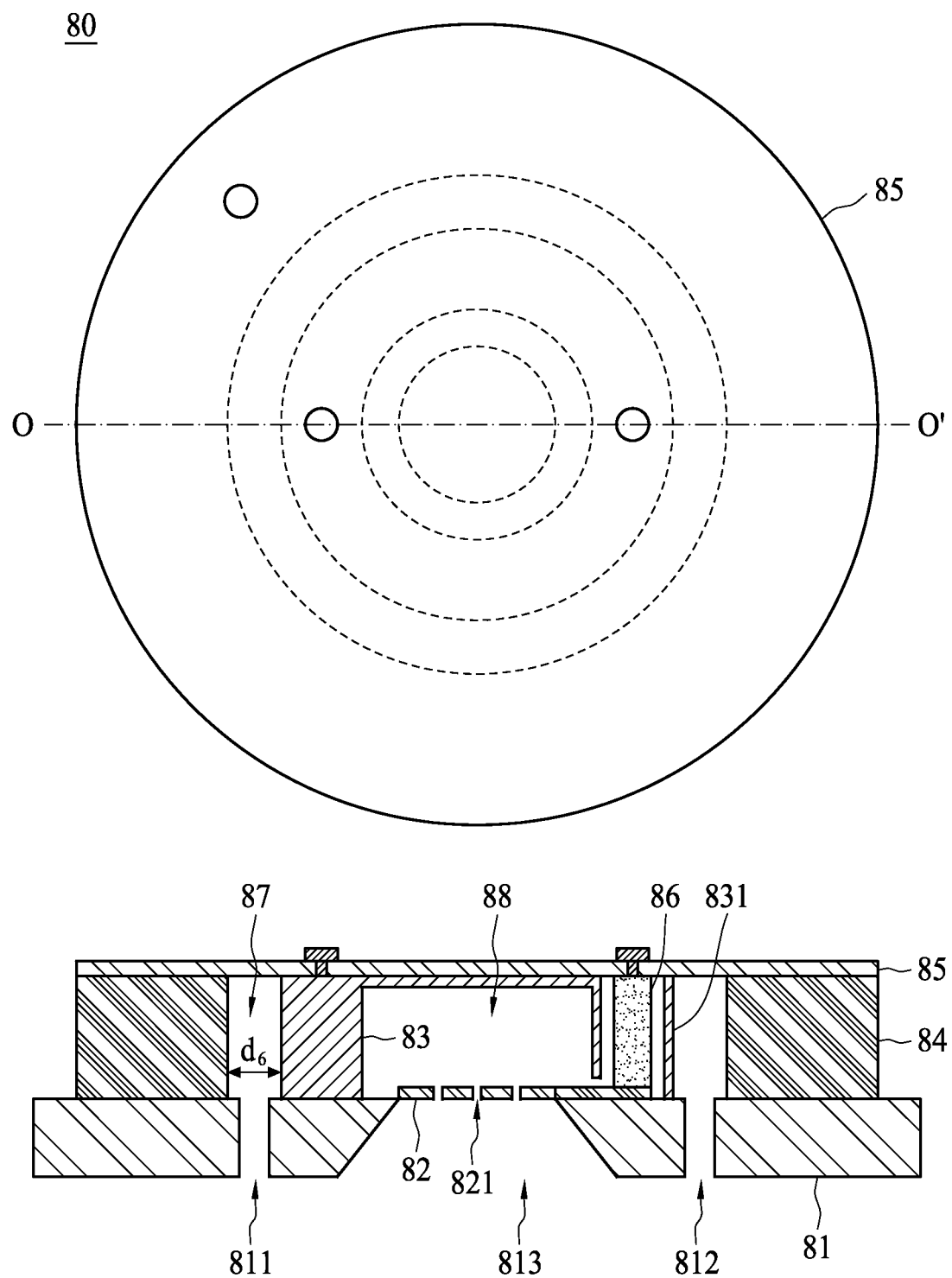
Figure 26:
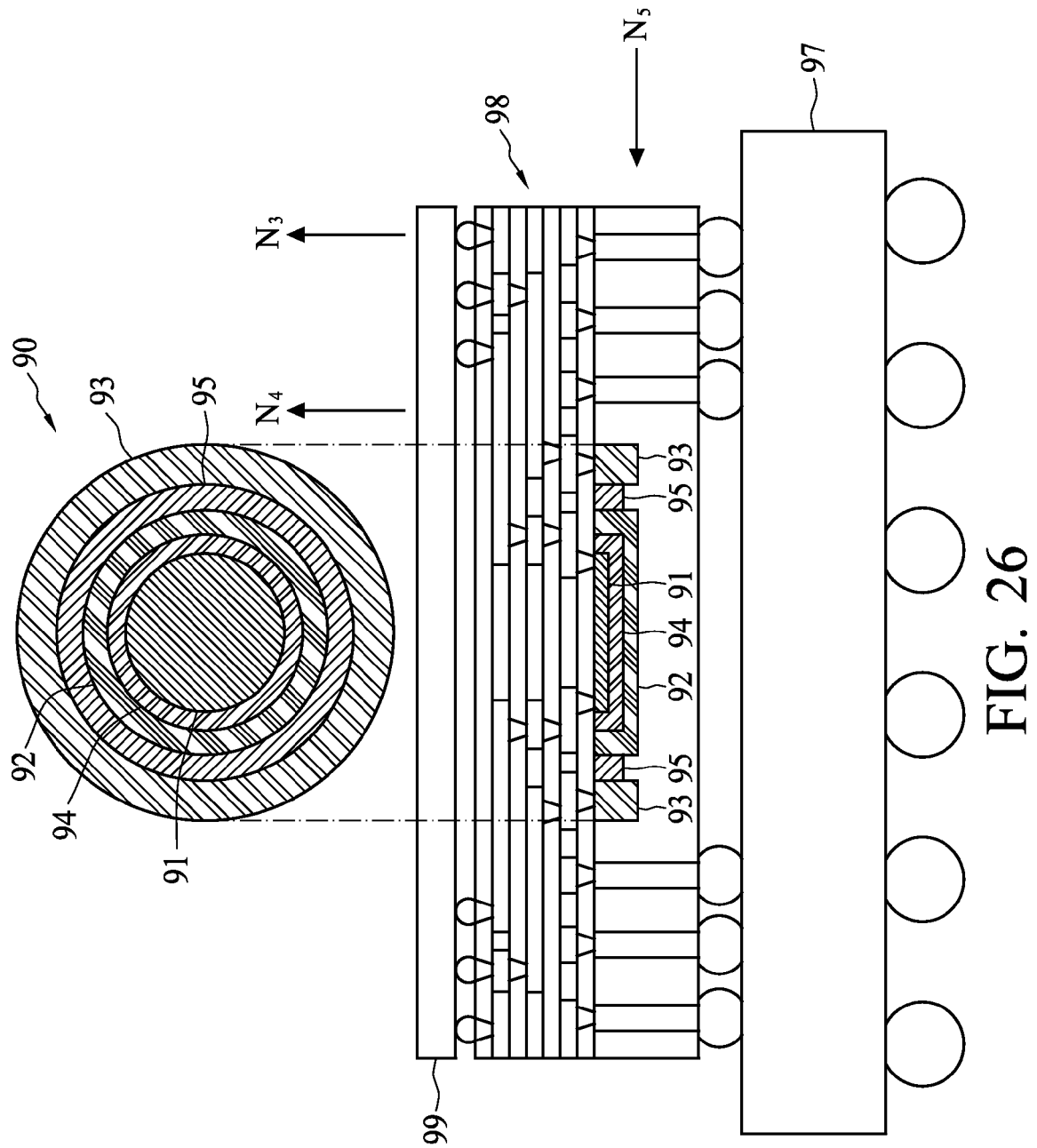
Figure 27:
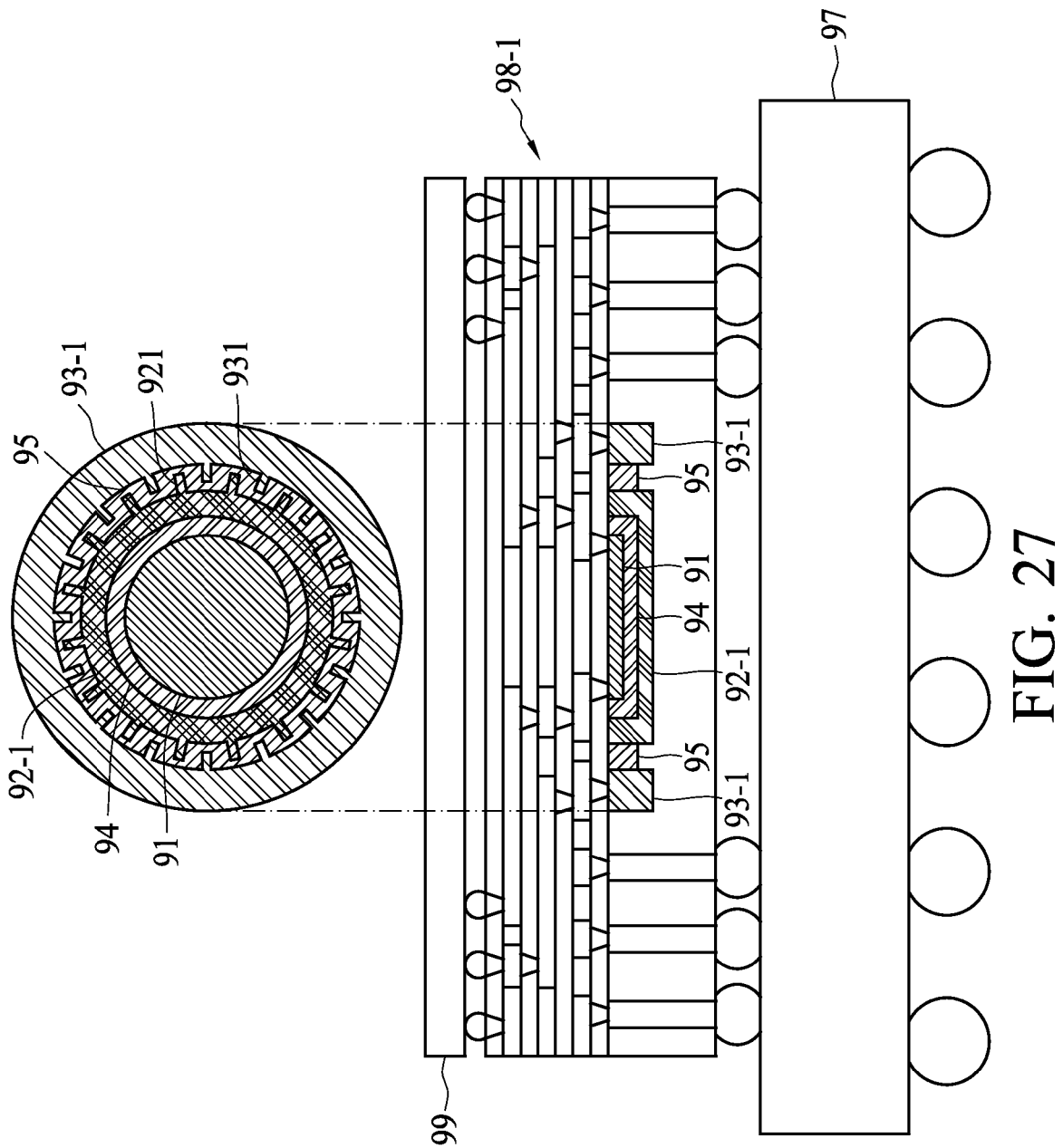
Figure 28:
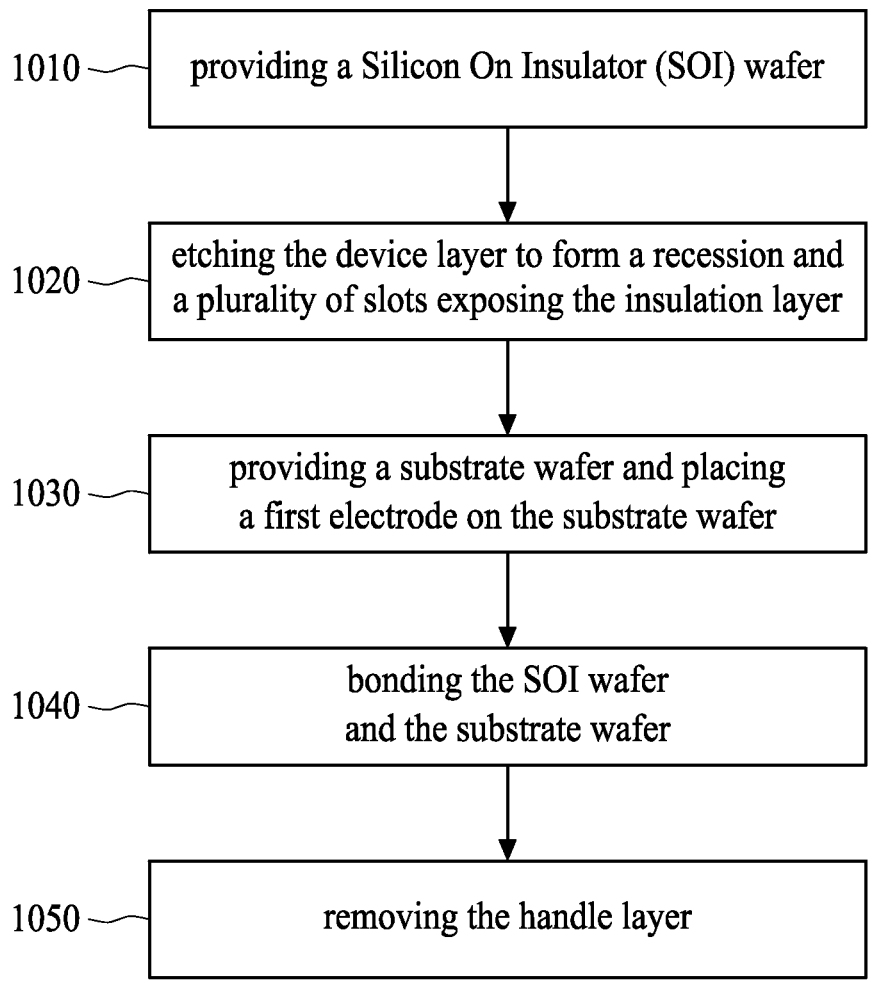

A more complete understanding of the present disclosure may be derived by referring to the detailed description and claims when considered in connection with the Figures, where like reference numbers refer to similar elements throughout the Figures, and:

FIG. 1 is a cross-sectional view of a conventional air-pressure sensor;

FIG. 2 is a cross-sectional view illustrating a conventional air-pressure sensor pushed by an external air pressure $P_2$;

FIG. 3 is a cross-sectional view of a conventional differential pressure sensor;

FIG. 4 is a top view of the conventional differential pressure sensor illustrated in FIG. 3;

FIG. 5 is a cross-sectional view of an upper portion and a bottom portion of another conventional differential pressure sensor;

FIG. 6 is a cross-sectional view of a MEMS device with multiple electrodes in accordance with one embodiment of the present disclosure;

FIG. 7 is a cross-sectional view of a MEMS device with multiple electrodes in accordance with another embodiment of the present disclosure;

FIG. 8 is a top view of a MEMS device in accordance with another embodiment of the present disclosure;

FIG. 9 is a cross-sectional view of the MEMS device taken along the line A-A' in FIG. 8 in accordance with an embodiment of the present disclosure;

FIG. 10 is a cross-sectional view of the MEMS device taken along the line B-B' in FIG. 9 in accordance with an embodiment of the present disclosure;

FIG. 11 is a cross-sectional view of the MEMS device taken along the line C-C' in FIG. 9 in accordance with an embodiment of the present disclosure;

FIG. 12 is a cross-sectional view of the MEMS device taken along the line D-D' in FIG. 8 embodiment of the present disclosure;

FIG. 13 is a cross-sectional view of a modified MEMS device derived from FIG. 8 taken along the line F-F' in accordance with an embodiment of the present disclosure;

FIG. 14 is a cross-sectional view of a modified MEMS device derived from FIG. 13 taken along the line G-G' in accordance with an embodiment of the present disclosure;

FIG. 15 is a top view of a MEMS device in accordance with another embodiment of the present disclosure;

FIG. 16 is a cross-sectional view of the MEMS device taken along the line E-E' in FIG. 15 in accordance with an embodiment of the present disclosure;

FIG. 17 is a top view of a MEMS device in accordance with another embodiment of the present disclosure;

FIG. 18 is a cross-sectional view of the MEMS device taken along the line H-H' in FIG. 17 in accordance with an embodiment of the present disclosure;

FIG. 19 is a cross-sectional view of the MEMS device taken along the line J-J' in FIG. 19 in accordance with an embodiment of the present disclosure;

FIG. 20 is a cross-sectional view of the MEMS device taken along the line K-K' in FIG. 20 in accordance with an embodiment of the present disclosure;

FIG. 21 is a cross-sectional view of the MEMS device taken along the line L-L' in FIG. 21 in accordance with an embodiment of the present disclosure;

FIG. 22 is a cross-sectional view of the MEMS device taken along the line I-I' in FIG. 22 in accordance with an embodiment of the present disclosure;

FIG. 23 illustrates a top view and a cross-sectional view of the MEMS device taken along the line M-M' in FIG. 23 in accordance with another embodiment of the present disclosure;

FIG. 24 illustrates a top view and a cross-sectional view of the MEMS device taken along the line N-N' in FIG. 24 in accordance with another embodiment of the present disclosure;

FIG. 25 illustrates a top view and a cross-sectional view of the MEMS device taken along the line O-O' in FIG. 25 in accordance with another embodiment of the present disclosure;

FIG. 26 illustrates a top view and a cross-sectional view taken along the MEMS device applied for silicon interposer in accordance with another embodiment of the present disclosure;

FIG. 27 illustrates a top view and a cross-sectional view of a modified MEMS device derived from FIG. 26 in accordance with an embodiment of the present disclosure;

FIG. 28 is a flow chart of a fabricating method of a MEMS device in accordance with an embodiment of the present disclosure; and FIGS. 29 to 37 are schematic views illustrating a method of fabricating a MEMS device in accordance with one embodiment of the present disclosure.

DETAILED DESCRIPTION

The present disclosure is directed to a MEMS device with multiple electrodes and a fabricating method thereof. In order to make the present disclosure completely comprehensible, detailed steps and structures are provided in the following description. Obviously, implementation of the present disclosure does not limit special details known by persons skilled in the art. In addition, known structures and steps are not described in details, so as not to limit the present disclosure unnecessarily. Preferred embodiments of the present disclosure will be described below in detail. However, in addition to the detailed description, the present disclosure may also be widely implemented in other embodiments. The scope of the present disclosure is not limited to the detailed embodiments, and is defined by the claims. The following description of the disclosure accompanies drawings, which are incorporated in and constitute a part of this specification, and illustrate embodiments of the disclosure, but the disclosure is not limited to the embodiments.

In addition, the following embodiments can be properly integrated to complete another embodiment. References to "modified embodiment," "the embodiment," "other embodiments," "another embodiment," etc. indicate that the embodiment(s) of the disclosure so described may include a particular feature, structure, or characteristic, but not every embodiment necessarily includes the particular feature, structure, or characteristic. Further, repeated use of the phrase "in the embodiment" does not necessarily refer to the same embodiment, although it may.

In addition, unless specifically stated otherwise, as apparent from claims and detailed description, it is appreciated that throughout the specification the quantity of components is single. If the quantity of the labeled component is one, the quantifier is explained to include one unit or at least one unit. If the quantity of the labeled component is a plurality, the quantifier is explained to include at least two units.

The following description of the disclosure accompanies drawings, which are incorporated in and constitute a part of this specification, and illustrate embodiments of the disclosure, but are not limited to the embodiments. In addition, the following embodiments can be properly integrated to complete another embodiment.

FIG. 6 is a cross-sectional view of a MEMS device 10 with multiple electrodes in accordance with one embodiment of the present disclosure. In the embodiment shown in FIG. 6, the MEMS device 10 with multiple electrodes includes a substrate 11, a first electrode 12, a second electrode 13 and a third electrode 14.

In the present embodiment, the first electrode 12 is a circular plate. However, in other embodiments (not shown), the first electrode 12 may be designed with other geometric shapes corresponding to the shape of the second electrode 13. As shown in FIG. 6, the first electrode 12 is disposed on a top surface 111 of the substrate 11. When the MEMS device 10 with multiple electrodes measures the air pressure, the substrate 11 does not deform. Thus, the first electrode 12 disposed on the substrate 11 may be regarded as a stationary electrode used for sensing the air pressure.

In the present embodiment, the second electrode 13 is a circular cover. However, in other embodiments (not shown), the second electrode 13 may be designed with other geometric shapes, such as square cover, corresponding to the shape of the third electrode 14. As shown in FIG. 6, the second electrode 13 is disposed on the substrate 11. In the specification and the contemplated scope of protection, the term "on" means that a first member is directly or indirectly disposed above the second member. For instance, in the embodiment that the second electrode 13 is disposed on the substrate 11, the second electrode 13 in one example is directly disposed on the substrate 11, and in another example is indirectly disposed above the substrate 11. The term "indirectly" means that in a vertical view, two members are disposed at an upper position and a lower position, respectively, while other objects, material layers or gaps are disposed between the two members.

The second electrode 13 includes a sensing portion 131 and a stationary portion 132. When the MEMS device 10 with multiple electrodes detects air pressure, the sensing portion 131 deforms. Thus, the sensing portion 131 of the second electrode 13 and the first electrode 12 define a variable capacitor which may be also called a sensing capacitor.

In the present embodiment, the stationary portion 132 is a ring structure. However, in other embodiments (not shown), the shape of the stationary portion 132 may be designed with other geometric shapes corresponding to the shape of the third electrode 14 or the first electrode 12. As shown in FIG. 6, the stationary portion 132 is disposed on the top surface 111 while the stationary portion 132 connects the sensing portion 131. Accordingly, the stationary portion 132 is configured to separate the first electrode 12 and the sensing portion 131 and form a gap. Furthermore, one end of the stationary portion 132 is disposed on the top surface 111 of the substrate 11 and the other end of the stationary portion 132 connects with the periphery of the sensing portion 131.

The third electrode 14 is disposed on the top surface 111 of the substrate 11. In the embodiment, the third electrode 14 may be shaped into a ring. However, in other embodiment (not shown), the shape of the third electrode 14 may designed as other geometric shapes, such as square ring, corresponding to the shape of the third electrode 14 or the first electrode 12.

When the MEMS device 10 with multiple electrodes measures air pressure, the stationary portion 132 and the third electrode 14 do not deform. Thus, the stationary portion 132 and the third electrode 14 are spaced apart by a predetermined constant distance $d_2$. In other words, when the sensing portion 131 of the second electrode 13 deforms, the predetermined constant distance $d_2$ between the stationary portion 132 and the third electrode 14 still maintains as a constant. In addition, the stationary portion 132 and the third electrode 14 define a reference capacitor. Since the distance between the stationary portion 132 and the third electrode 14 is constant, the reference capacitor is also called a stationary capacitor.

Since the second electrode 13 has same electrical voltage, the voltage potential of the stationary portion 132 is identical to the voltage potential of the sensing portion 131. The sensing portion 131 and the first electrode 12 may form the sensing capacitor. The stationary portion 132 and the third electrode 14 may form the reference capacitor.

The stationary portion 132 surrounds the first electrode 12 while the third electrode 14 surrounds the second electrode 13. Since the sensing capacitor defined between the first electrode 12 and the sensing portion 131 and the reference capacitor defined between the stationary portion 132 and the third electrode 14 are disposed in an area which is surrounded by the third electrode 14, it is possible for the MEMS device 10 with multiple electrodes to be shrunk so as to meet the requirement of miniaturization of the mobile electronics.

The second electrode 13 is configured to seal the first electrode 12. In other words, after the second electrode 13 connects with the substrate 11, the second electrode 13 and the substrate 11 will define a first space 15 where the first electrode 12 is disposed. In the embodiment, the first space 15 is a hermetic space, which encloses the first electrode. However, in other embodiments (not shown), the first space 15 is not limited to the hermetic space and the first space 15 can be non-hermetic for different designs.

In the specification and the scope of protection, the term "hermetic space" may be defined as follows. Under the method (MIL-STD-883E method 1014.9) of detecting gas density, after the sample device with the first space is placed at a chamber filled with helium gas (75±2 psia) for two hours, the sample device is located at a vacuum situation and is detected to calculate the ratio of leaking helium gas. If the leaking ratio is less than the standard ($5 \times 10^{-8}$ atm cc/sec), the first space in the sample device can be termed as a hermetic space.

FIG. 7 is a cross-sectional view of a MEMS device 20 with multiple electrodes in accordance with another embodiment of the present disclosure. In the embodiment shown in FIG. 7, the MEMS device 20 with multiple electrodes includes a substrate 21, a first electrode 22, a second electrode 23 and a third electrode 24.

The first electrode 22 is disposed on the substrate 21. The second electrode 23 and the first electrode 22 are configured to define a sensing capacitor $C_1$. Since the first electrode 22 faces the sensing portion 231 of the second electrode 23, the pointing direction $N_1$ of the first electrode 11 is in parallel with the normal direction N of the substrate 21.

The second electrode 23 includes a sensing portion 231 and a stationary portion 232. The third electrode 24 is disposed on the substrate 21 and configured to form a reference capacitor $C_2$, which is also called a stationary capacitor. Moreover, the stationary portion 232 of the second electrode 23 faces the third electrode 24. The pointing direction $N_1$ of the first electrode 22 is perpendicular to the pointing direction $N_2$ of the third electrode 24. However, in some embodiments, the fabricating process for the MEMS device may cause error or tolerance which affects the right angle between the pointing direction of the first electrode 22 and the pointing direction of the third electrode 24 so that the angle between these two directions ranges from 89° to 91°. In the embodiment shown in FIG. 7, the MEMS device 20 with multiple electrodes further includes an electrical insulation layer 25 which covers the second electrode 23 and the third electrode 24. In the embodiment, the electrical insulation layer 25 may be, but not limited to, a circular plate. However, in other embodiments (not shown), the electrical insulation layer 25 may be designed with other shapes, such as a square. As shown in FIG. 7, the electrical insulation layer 25 connects the sensing portion 231 of the second electrode 23 and the third electrode 24. In other words, the electrical insulation layer 25 does not directly connect with the first electrode 22. In addition, the sensing portion 231 of the sensing capacitor $C_1$ and the stationary portion 232 of the reference capacitor $C_2$ both are located at the second electrode 23 having the same electric potential.

The electrical insulation layer 25, the stationary portion 232, the third electrode 24 and the top surface 211 of the substrate 21 define a second space 26. In the embodiment, the second space 26 is a hermetic space. However, in other embodiments (not shown), the second space 26 may be a non-hermetic space. For example, the second space 26 may be filled with dielectric material.

The stationary portion 232 includes a through hole 233. The MEMS device 20 with multiple electrodes further includes a conductive post 27, which is disposed inside the through hole 233 and is electrically coupled to the first electrode 22. Moreover, the first electrode 22 further includes an extension terminal 221, which is electrically coupled to the conductive post 27. Thus, the voltage potential of the conductive post 27 is identical with the voltage potential of the first electrode 22.

Furthermore, the stationary portion 232 and the conductive post 27 are electrically conductive material. In order to avoid electric short between the sensing portion 231 of the second electrode 23 and the first electrode 22, the conductive post 27 and the stationary portion 232 are spaced apart by a gap. As a result, the conductive post 27 is electrically insulated from the stationary portion 232. Furthermore, the sensing portion 231 further includes a hole 235 connecting the through hole 233. The hole 235 is configured to accommodate the conductive post 27. Accordingly, the conductive post 27 is electrically insulated from the sensing portion 231.

In the embodiment shown in FIG. 7, one end of the stationary portion 232 is disposed on the top surface 211 of the substrate 21 and the other end of the stationary portion 232 connects with the periphery of the sensing portion 231. In some embodiments, the second electrode 23 and the electrical insulation layer 25 are configured to seal the first electrode 22. In some embodiments, the second electrode 23 covered by the electrical insulation layer 25 is connected with the substrate 21 to form a first space 28. In the embodiment of the present disclosure, the first space 28 may be a hermetic space, which encloses the first electrode 22.

Furthermore, the first space 28 in one example is filled with gas to serve as a sensor for detecting relative pressure, and in another example is kept in vacuum to serve as a sensor for measuring absolute pressure. As shown in FIG. 7, when the air-pressure $P_3$ of the first space 28 is smaller than the external air-pressure $P_4$, the sensing portion 231 and the electrical insulation layer 25 disposed on the sensing portion 231 will deform forward the first electrode 22. If the internal air-pressure $P_3$ is greater than the external air-pressure $P_4$, the sensing portion 231 and the electrical insulation layer 25 disposed on the sensing portion 231 will deform away from the first electrode 22. Shortly, the deforming direction of the sensing portion 231 of the second electrode 23 is in parallel with the normal direction N of the substrate 21. The normal direction N is the same as the pointing direction $N_1$ of the first electrode 22.

The third electrode 24 surrounds the stationary portion 232 of the second electrode 23. In the embodiment, the stationary portion 232 includes a plurality of first protruding portions 234 while the third electrode 24 includes a plurality of second protruding portions 241. The first protruding portions 234 outwardly radiates from the stationary portion 232, but the second protruding portions 241 inwardly radiates toward the stationary portion 232. Thus, the first protruding portions 234 and the second protruding portions 241 are arranged to form an interdigital capacitor. When the MEMS device 20 with multiple electrodes detects air pressure, the stationary portion 232 and the third electrode 24 do not deform. Thus, the distance $d_3$ between the first protruding portions 234 and the second protruding portions 241 is constant. Moreover, the first protruding portions 234 and the second protruding portions 241 will increase the charged area of the reference capacitor $C_2$ so as to increase total capacitance thereof.

FIG. 8 is a top view of a MEMS device 30 of the present disclosure. In the embodiment shown in FIG. 8, the electrical insulation layer 35 includes a plurality of electrical contacts 351, 352 and 353.

FIG. 9 illustrates a cross-sectional view of the MEMS device 30 taken from the line A-A' in FIG. 8. As shown in FIG. 9, the MEMS device 30 with multiple electrodes includes a substrate 31, a first electrode 32, a second electrode 33, a third electrode 34, an electrical insulation layer 35 and a conductive post 37.

The first electrode 32, the second electrode 33 and the third electrode 34 are disposed on the substrate 31. The stationary portion 331 of the second electrode 33 is peripherally disposed around the first electrode 32. In other words, the stationary portion 331 of the second electrode 33 surrounds the first electrode 32. In addition, the third electrode 34 is peripherally disposed around the second electrode 33 and surrounds the second electrode 33. Therefore, the third electrode 34 also surrounds the first electrode 32.

In the embodiment shown in FIG. 9, since the first electrode 32 faces the sensing portion 332 of the second electrode 33, the pointing direction of the first electrode 32 is in parallel with the normal direction N of the substrate 31. Moreover, because the stationary portion 331 faces the third electrode 34, the pointing direction of the third electrode 34 is perpendicular to the pointing direction of the first electrode 32. In the embodiment, the included angle between the pointing direction of the third electrode 34 and the pointing direction of the first electrode 32 is substantially 90°.

As shown in FIG. 9, the first electrode 32 is disposed on the top surface 311 of the substrate 31. Since the stationary portion 331 supports the sensing portion 332, the sensing portion 332 and the first electrode 32 are spaced apart by a distance $d_4$. The distance $d_4$ allows the sensing portion 332 and the first electrode 32 to form a sensing capacitor $C_3$. When the MEMS device 30 measures air pressure or altitude, the sensing portion 332 will deform to change the distance $d_4$. Since the capacitance of the sensing capacitor $C_3$ will changes due to the variation of the distance $d_4$, the sensing capacitor $C_3$ is a variable capacitor. When the MEMS device 30 measures air pressure or altitude, the stationary portion 331 and the third electrode 34 do not deform. Thus, the distance $d_5$ between the stationary portion 331 and the third electrode 34 does not change due to variation of air pressure. The constant distance $d_5$ allows the stationary portion 331 and the third electrode 34 to form a reference capacitor $C_4$ (also called a stationary capacitor). In the embodiment, the electric-field direction of the sensing capacitor $C_3$ is substantially perpendicular to the electric-field direction of the reference capacitor $C_4$.

A lower drawing of FIG. 10 illustrates a cross-sectional view of the MEMS device 30 taken from the line B-B' of FIG. 10. As shown in FIG. 10, the second electrode 33 includes a through hole 36. Referring to FIG. 10, the conductive post 37 is disposed inside the through hole 36. The conductive post 37 does not contact the second electrode 33. In the embodiment, the electrical insulation layer 35 includes a first conductive through hole 354 and a second conductive through hole 355.

In the specification and patent scope of the present disclosure, the term "conductive through hole" is defined as a through hole which is filled with electrically conductive material. Thus, the conductive through hole has characteristic of the electrical conductor. The first conductive through hole 354 connects with the conductive post 37. Therefore, the electrical signal may be transmitted from the electrical contact 351 to the conductive post 37 through the first conductive through hole 354, vice versa. In other words, the electrical signal may be transmitted from the conductive post 37 to the electrical contact 351 through the first conductive through hole 354.

A lower drawing of FIG. 11 illustrates a cross-sectional view of the MEMS device 30 taken from the line C-C' of FIG. 11. In the embodiment shown in FIG. 11, the conductive post 37 connects to the extension terminal 321 of the first electrode 32. Thus, the electrical signal can be transmitted to the first electrode 32 through the electrical contact 351, the first conductive through hole 354, the conductive post 37 and the extension terminal 321, vice versa. In other words, the electrical signal can be transmitted from the first electrode 32 to the electrical contact 351. Since the through hole 36 and the hole 361 keep the extension terminal 321 from connecting the stationary portion 331 of the second electrode 33, the first electrode 32 is electrically insulated from the second electrode 33.

In the embodiment, the second electrode 33 is electrically coupled to the electrical contact 352 through the second conductive through hole 355. Thus, the electrical signal is transmitted from the electrical contact 352 to the second electrode 33 through the second conductive through hole 355, vice versa. In other words, the electrical signal may be transmitted from the second electrode 33 to the electrical contact 352.

A lower drawing of FIG. 12 illustrates a cross-sectional view of the MEMS device 30 taken from the line D-D' of FIG. 12. In the embodiment shown in FIG. 12, the electrical contact 353 is electrically coupled to the third electrode 34 through the third conductive through hole 356. Thus, referring FIG. 9, individual electrical signals can be respectively transmitted to the first electrode 32, the second electrode 33 and the third electrode 34 through the electrical contact 351, 352 and 353.

Moreover, in other embodiments (not shown), the second electrode 33 may include the first protruding portions 234 shown in FIG. 7, while the third electrode 34 may include the second protruding portions 241 shown in FIG. 7. Thus, the first protruding portions 234 and the second protruding portions 241 are arranged to form an interdigital capacitor.

Referring FIG. 12, the sensing portion 332, the stationary portion 331 and the substrate 31 define a first space 38, which is a hermetic space enclosing the first electrode 32. However, in other embodiment (not shown), the first space 38 may be designed to be a non-hermetic space in accordance with other requirements.

In the embodiment shown in FIG. 12, the electrical insulation layer 35 connects with the second electrode 33 and the third electrode 34. Moreover, the electrical insulation layer 35, the stationary portion 331, the third electrode 34 and the substrate 31 define the second space 39 which is a hermetic space. However, in other embodiments (not shown), the second space 39 may be designed as a non-hermetic space in accordance with different designs.

In other embodiments (not shown), the MEMS device 30 further includes a dielectric material which is filled into the second space 39 to increase the capacitance. In some embodiments, the dielectric material may be selected from $SiO_2$, $Si_3N_4$ and a mixture thereof.

FIG. 13 illustrates a modified embodiment derived from the embodiment shown in FIG. 8. The upper portion of FIG. 13 illustrates the top view of the MEMS device 30, while the lower portion of FIG. 13 shows the cross-sectional view of the modified MEMS device taken from the line F-F' in FIG. 13. As shown in FIG. 13, the electrical insulation layer 35 of the MEMS device 30 connects partial sensing portion 332 of the second electrode 33. In the embodiment, through removing partial electrical insulation layer 35 disposed on the sensing portion 332, the MEMS device 30 of the present disclosure may reduce the residual stress of the sensing portion 332 so as to increase the accuracy for detecting the pressure.

FIG. 14 illustrates a modified embodiment derived from the embodiment shown in FIG. 13. The upper portion of FIG. 14 illustrates the top view of the MEMS device 30, while the lower portion of FIG. 14 shows the cross-sectional view of the modified MEMS device taken from the line G-G' in FIG. 14. As shown in FIG. 14, the MEMS device 30 further includes a second conductive layer 357, which is disposed on the sensing portion 332 where the electrical insulation layer is not disposed. The second conductive layer 357 is then electrically coupled to the electric contact 352. Under the electric contact 352, there is no conductive through hole penetrating the electrical insulation layer 35. Thus, the sensing portion 332 is electrically coupled to the electrical contact 352 through second conductive layer 357.

FIG. 15 illustrates the top view of the MEMS device 40. FIG. 16 is a cross-sectional view of the MEMS device 40 taken from the line E-E' in FIG. 15. In the embodiment shown in FIG. 16, the MEMS device 40 further includes a substrate 41, a first electrode 42, a second electrode 43, a third electrode 44, an electrical insulation layer 45 and a first conductive layer 46.

In the embodiment, the substrate 41, the first electrode 42, the second electrode 43, the third electrode 44 and the electrical insulation layer 45 are similar to the substrate 31, the first electrode 32, the second electrode 33, the third electrode 34 and the electrical insulation layer 35 shown in FIGS. 8 and 9.

In view of FIG. 16, the first conductive layer 46 is disposed on the electrical insulation layer 45. The first conductive layer 46 is configured to remove the excess electric charge in the electrical insulation layer 45 so as to avoid the interference on the sensing capacitor between the first electrode 42 and the second electrode 43. In the embodiment, the structure and connecting relationship of the electrical contacts 451, 452, 453 are similar to those of the electrical contacts 351, 352, 353 shown in FIG. 8 and FIG. 12. As shown in FIGS. 15 and 16, the first conductive layer 46 is electrically coupled to the electrical contact 454 which is grounded to remove the excess electric charge in the electrical insulation layer 45. In other words, the electric contacts 451, 452 and 453 are electrically insulated from the first conductive layer 46. Thus, the electrical contacts 451, 452 and 453 can be used to transmit electrical signal to the first electrode 42, the second electrode 43 and the third electrode 44, respectively.

FIG. 17 is the top view of the MEMS device 50. FIG. 18 is a cross-sectional view of the MEMS device 50 taken from the line H-H' in FIG. 17. In the embodiment shown in FIG. 18, the MEMS device 50 includes the substrate 51, the first electrode 52, the second electrode 53, the third electrode 54, the electrical insulation layer 55, a plurality of through holes 561, 562, 563, a plurality of conductive posts 571, 572, 573 and the integrated circuit chip 58. In order to describe the location and the connecting relationship of the conductive posts 571, 572, 573, the conductive post 572, 573 disposed inside the third electrode 54 may be also called the first conductive posts 572, 573.

In the embodiment, the substrate 51 may be a glass substrate or other dielectric substrate. The integrated circuit chip 58 is disposed on a bottom surface of the substrate 51.

The first electrode 52 is disposed on the substrate 51 and includes an extension terminal 521 which connects to the conductive post 571 which is disposed inside the through hole 561. The electrical insulation layer 55 further includes a plurality of conductive through holes 551, 552, 553 and 554. The external conductive trace 556 is disposed on the electrical insulation layer 55 and connects to the conductive through holes 551 and 552. The conductive through hole 552 connects with the first conductive post 573 which is disposed inside the through hole 563. In other words, a conductive through hole 551 in the electrical insulation layer 55 connects with the conductive post 571 and the external conductive trace 556. Another conductive through hole 552 in the electrical insulation layer 55 connects with the external conductive trace 556 and the first conductive post 573.

The first conductive post 573 is disposed inside the third electrode 54 and electrically insulated from the third electrode 54. Similarly, the external conductive trace 557 is disposed on the electrical insulation layer 55 and connects with the conductive through holes 553 and 554. The conductive through hole 554 connects with the first conductive post 572 which is disposed inside the through hole 562. In other words, the first conductive post 572 is disposed inside the third electrode 54 and electrically insulated from the third electrode 54. A lower drawing of FIG. 19 illustrates a cross-sectional view of the MEMS device 50 taken from the line J-J' of FIG. 19. As shown in FIG. 19, the conductive post 571 is disposed inside the through hole 561. The first conductive post 572 is disposed inside the through hole 562. The first conductive post 573 is disposed inside the through hole 563. Thus, the conductive post 571 is electrically insulated from the second electrode 53. The first conductive post 572 is electrically insulated from the third electrode 54. The first conductive post 573 is electrically insulated from the third electrode 54.

A lower drawing of FIG. 20 illustrates a cross-sectional view of the MEMS device 50 taken from the line K-K' of FIG. 20. As shown in FIGS. 18 and 20, an electrical isolation layer 592 is disposed on a bottom surface 541 of the third electrode 54. The electrical isolation layer 592 further includes a plurality of conductive through holes 594 and 595. In the embodiment, the electrical isolation layer 592 surrounds the conductive through holes 594 and 595 which are electrically insulated from the third electrode 54.

A lower drawing of FIG. 21 illustrates a cross-sectional view of the MEMS device 50 taken from the line L-L' of FIG. 21. As shown in FIGS. 18 and 21, the conductive trace layers 591 and 593 are disposed below the electrical isolation layer 592. Partial the conductive trace layers 591 and 593 are disposed between the electrical isolation layer 592 and the substrate 51. Since the conductive through hole 594 connects with the conductive trace layer 591 and the first conductive post 573, the conductive trace layer 591 can transmit the electrical signal to the first conductive post 573.

Similarly, since the conductive through hole 595 connects with the conductive trace layer 593 and the first conductive post 572, the conductive trace layer 593 may transmit the electrical signal to the first conductive post 572.

As shown in FIG. 18, the conductive through hole 594 connects with the first conductive post 573 and the conductive trace layer 591. The integrated circuit chip 58 is disposed on the bottom surface 511 of the substrate 51. The conductive bump 582 is disposed on the integrated circuit chip 58. The integrated circuit chip 58 is electrically coupled to the first conductive post 573. In some embodiments, the bonding wire 581 connects with the conductive trace layer 591 and the conductive bump 582. Thus, the conductive bump 582 disposed on the integrated circuit chip 58 is electrically coupled to the conductive trace layer 591 through the conductive wire 581 so as to be electrically coupled to the first conductive post 573. Therefore, the first electrical signal from the integrated circuit chip 58 is transmitted to the first electrode 52 through the conductive bump 582, the conductive wire 581, the conductive trace layer 591, the conductive through hole 594 in the electrical isolation layer 592, the first conductive post 573, the conductive through hole 552 in the electric insulation layer 55, the external conductive trace 556, the conductive through hole 551 in the electric insulation layer 55, the conductive post 571, the extension terminal 521, vice versa. In other words, the first electrical signal is transmitted from the first electrode 52 to the conductive bump 582.

As shown in FIG. 18, the second electrode 53 is connected to the conductive through hole 553. The external conductive trace 557 is connected with the conductive through holes 553 and 554. Thus, the second electrode 53 is electrically coupled to the first conductive post 572. The first conductive post 572 is electrically coupled to the conductive trace layer 593 through the conductive through hole 595. The conductive trace layer 593 and the conductive bump 583 is connected through the conductive wire 584. In some embodiments, the second electrical signal of the integrated circuit chip 58 can be transmitted from the conductive bump 583 to the second electrode 53 through the conductive wire 584, the conductive trace layer 593, the conductive through hole 595, the first conductive post 572, the conductive through hole 554, the external conductive trace 557, the conductive through hole 553, vice versa. In other words, the second electrical signal can be transmitted form the second electrode 53 to the conductive bump 583. In the embodiment, since the first electrical signal path is electrically insulated form the second electric signal path, the first electrical signal won't be transmitted to the second electrode, vice versa.

A lower drawing of FIG. 22 illustrates a cross-sectional view of the MEMS device 50 taken from the line I-I' of FIG. 22. In the embodiment shown in FIGS. 18 and 22, since the third electrode 54 connects with the conductive through hole 597 in the electrical isolation layer 592, the third electrode 54 is electrically coupled to the conductive trace layer 596. The conductive trace layer 596 and the conductive bump 585 is electrically coupled through the conductive wire 586. In some embodiments, the third electrical signal of the integrated circuit chip 58 may be transmitted from the conductive bump 585 to the third electrode 54 through the conductive wire 586, the conductive trace layer 596, the conductive through hole 597, vice versa. In other words, the third electrical signal could be transmitted from the third electrode 54 to the conductive bump 585. In the embodiment, since the third electrical signal path is electrically insulated form the first electrical signal path or the second electrical signal path, the third electrical signal won't be transmitted to the first electrode or the second electrode, respectively.

In summary, the first conductive post 573 is disposed inside the third electrode 54 and electrically insulated from the third electrode 54. The external conductive trace 556 is disposed on the electric insulation layer 55 which includes conductive through holes 551 and 552. The electrical isolation layer 592 is disposed on the bottom surface 541 of the third electrode 54 and includes another conductive through hole 594. Furthermore, the conductive trace layers 591 and 593 are disposed below the electrical isolation layer 592. Partial conductive trace layers 591 and 593 are disposed between the electrical isolation layer 592 and the substrate 51. The conductive bump 582 is disposed on the integrated circuit chip 58. In order to allow the integrated circuit chip 58 to be electrically coupled to the conductive post 571 and the first electrode 52, the connecting relations are built as followings: A conductive through hole 551 in the electrical insulation layer 55 connects with the conductive post 571 and the external conductive trace 556. Another conductive through hole 552 in the electrical insulation layer 55 connects the external conductive trace 556 and the first conductive post 573. The conductive through hole 594 in the electrical isolation layer 592 connects with the first conductive post 573 and the conductive trace layer 591. The conducting wire 581 connects with the conductive trace layer 591 and the conductive bump 582.

FIG. 23 illustrates a modified embodiment of the MEMS device 50. The upper drawing of FIG. 23 illustrates the top view of the MEMS device 60, while the lower drawing of FIG. 23 shows the cross-sectional view of the MEMS device 60 taken from the line M-M' in FIG. 23. As shown in FIG. 23, the MEMS device 60 includes a substrate 61, a first electrode 62, a second electrode 63, a third electrode 64, an electric insulation layer 65, a first conductive layer 66 and an integrated circuit chip 67. The first conductive layer 66 is disposed on the electric insulation layer 65 and configured to remove the excess electric charge in the electrical insulation layer 65 so as to avoid the interference on the sensing capacitor between the first electrode 62 and the second electrode 63 due to the accumulated charge.

As shown in FIG. 23, the first conductive layer 66 is connected to the electric contact 654 which is grounded to remove the excess electric charge in the electrical insulation layer 65. The external conductive traces 651 and 652 and the electric contact 653 are electrically insulated from the first conductive layer 66. Since the external conductive traces 651 and 652 and the electric contact 653 can transmit electrical signals to the first electrode 62, the second electrode 63 and the third electrode 64, respectively. Thus, the integrated circuit chip 67 can respectively transmit electrical signals to the first electrode 62, the second electrode 63 and the third electrode 64 through the external conductive traces 651, 652 and the electric contact 653.

FIG. 24 shows an embodiment of a MEMS device 70. The upper drawing of FIG. 24 illustrates the top view of the MEMS device 70, while the lower drawing of FIG. 24 shows the cross-sectional view of the MEMS device 70 taken from the line N-N' in FIG. 24. In the embodiment, the substrate of MEMS device 70 is an integrated circuit chip 71. As shown in FIG. 24, the MEMS device 70 includes the integrated circuit chip 71, a first electrode 72, a second electrode 73, a third electrode 74, an electrical insulation layer 75, a conductive layer 76 and a plurality of conductive posts 771 and 772. In order to describe the locations and the connecting relationship of the conductive posts 771 and 772, the conductive post 771 disposed inside the third electrode 74 is called a second conductive post 771.

The integrated circuit chip 71 further includes at least one conductive through holes 712, 713, 714 and 715 and at least one conductive bumps 716, 717, 718 and 719.

In the embodiment, the conductive bumps 716, 717, 718 and 719 are connected with t the conductive through holes 712, 713, 714 and 715, respectively. The conductive through holes 712, 713, 714, 715 are connected with the bonding layer 78, respectively. The conductive through holes 713, 714 and 715 are electrically coupled to the second electrode 73, the first electrode 72 and the third electrode 74 through the binding layer 78 respectively. In other words, the electrical signals of the conductive bumps 717, 718 and 719 are transmitted to the second electrode 73, the first electrode 72 and the third electrode 74 through the conductive through holes 713, 714 and 715 and the bonding layer 78 respectively.

As shown in FIG. 24, the conductive layer 76 is disposed on the electrical insulation layer 75 and configured to remove the accumulated electric charge in the electrical insulation layer 75 so as to avoid the interference on the sensing capacitor between the first electrode 72 and the second electrode 73.

In the embodiment, the second conductive post 771 is disposed inside the third electrode 74 and electrically insulated from the third electrode 74. The conductive bump 716 is electrically coupled to the second conductive post 771 through the conductive through hole 712 and the bonding layer 78. The second conductive post 771 is electrically coupled to the conductive layer 76 through the electrical contact 791. If the conductive bump 716 is grounded, the accumulated electric charge in the electrical insulation layer 75 can be removed.

FIG. 25 illustrates an embodiment of a MEMS device 80. The upper drawing of FIG. 25 illustrates the top view of the MEMS device 80, while the lower drawing of FIG. 25 shows the cross-sectional view of the MEMS device 80 taken from the line O-O' in FIG. 25. As shown in FIG. 25, the MEMS device 80 includes a substrate 81, a first electrode 82, a second electrode 83, a third electrode 84, an electric insulation layer 85, and the conductive post 86. The substrate 81 includes at least one openings 811, 812 and a back chamber 813. In the embodiment, the electrical insulation layer 85, the third electrode 84, the stationary portion 831 of the second electrode 83 and the substrate 81 define a second space 87. In the embodiment shown in FIG. 25, the at least one openings 811 and 812 communicate with the second space 87. In other words, the second space 87 of the embodiment is not a hermetic space.

In the embodiment, the back chamber 813 is disposed in the substrate 81 under the first electrode 82. In the embodiment, the second electrode 83, the substrate 81, the first electrode 82 and the electrical insulation layer 85 define a first space 88. The first electrode 82 further includes a plurality of apertures 821 by which the first space 88 can communicate with the back chamber 813. In other word, since the first space 88 can communicate with the back chamber 813 by apertures 821, the first space 88 is not a hermetic space. Thus, the MEMS device 80 of the present embodiment utilizes the back chamber 813, the apertures 821 and openings 811 and 812 to form a MEMS microphone.

In addition, since the distance $d_6$ between the stationary portion 831 and the third electrode 84 is not affected by sound wave, the stationary portion 831 and the third electrode 84 can form a reference capacitor. Therefore, the MEMS microphone of the present disclosure utilizes the differential design to reduce the noise.

In the embodiment shown in FIG. 26, a MEMS device 90 can be applied for Si-interposer 98. In 3-dimensional integrated circuit (3D-IC), Si-interposer 98 is disposed between the integrated circuit chip 99 and the substrate 97. For 3D-IC, the power integrity plays an important role in 3D-IC. In order to provide clean power, decouple capacitor is disposed close to the integrated circuit chip 99. The MEMS device of the present disclosure has multiple capacitors which is capable of providing decoupling function.

In the embodiment shown in FIG. 26, a MEMS device 90 of the present disclosure includes a first electrode 91, a second electrode 92 and a third electrode 93. The pointing direction ($N_4$) of the first electrode 91 is in parallel with the normal direction ($N_3$) of the Si-interposer 98. The pointing direction ($N_5$) of the third electrode 93 is perpendicular to the pointing direction ($N_4$) of the first electrode 91. The space between the first electrode 91 and the second electrode 92 may be filled with dielectric material 94. The dielectric material 94 can be oxide or nitride such as $SiO_2$ or $Si_3N_4$. Thus, the first electrode 91 and the second electrode 92 may form a first decoupling capacitor. In addition, the space between the second electrode 92 and the third electrode 93 may be filled with dielectric material 95. The dielectric material 95 can be oxide or nitride such as $SiO_2$ or $Si_3N_4$. Therefore, the second electrode 92 and the third electrode 93 may form a second decoupling capacitor. Furthermore, since the MEMS device 90 is disposed in the Si-interposer 98, the MEMS device 90 is surrounded by silicon.

The embodiment shown in FIG. 27 is a modified embodiment derived from the embodiment shown in FIG. 26. In the embodiment, the third electrode 93-1 further includes a plurality of second protruding portions 931. The second electrode 92-1 further includes a plurality of first protruding portions 921. The first protruding portions 921 and the second protruding portions 931 are arranged to form an interdigital capacitor. Because the second electrode 92-1 and the third electrode 93-1 do not deform, the distance between the first protruding portions 921 and the second protruding portions 931 is constant.

FIG. 28 illustrates a flow chart of fabricating method for a MEMS device. As shown in FIG. 28, the fabricating method includes following steps. The step 1010 provides a Silicon On Insulator (SOI) wafer which includes a device layer, an electrical insulation layer and a handle layer. The step 1020 etches the device layer to form recession and a plurality of slots exposing the electrical insulation layer. The step 1030 provides a substrate wafer and places a first electrode on the substrate wafer. The step 1040 bonds the substrate wafer and SOI wafer through wafer-to-wafer bonding process. Finally, the step 1050 removes the handle layer. The number of the step does not necessary mean the order of each steps.

The flow chart shown in FIG. 28 can be illustrated in following description relating to FIGS. 29 to 33.

Figure 29:
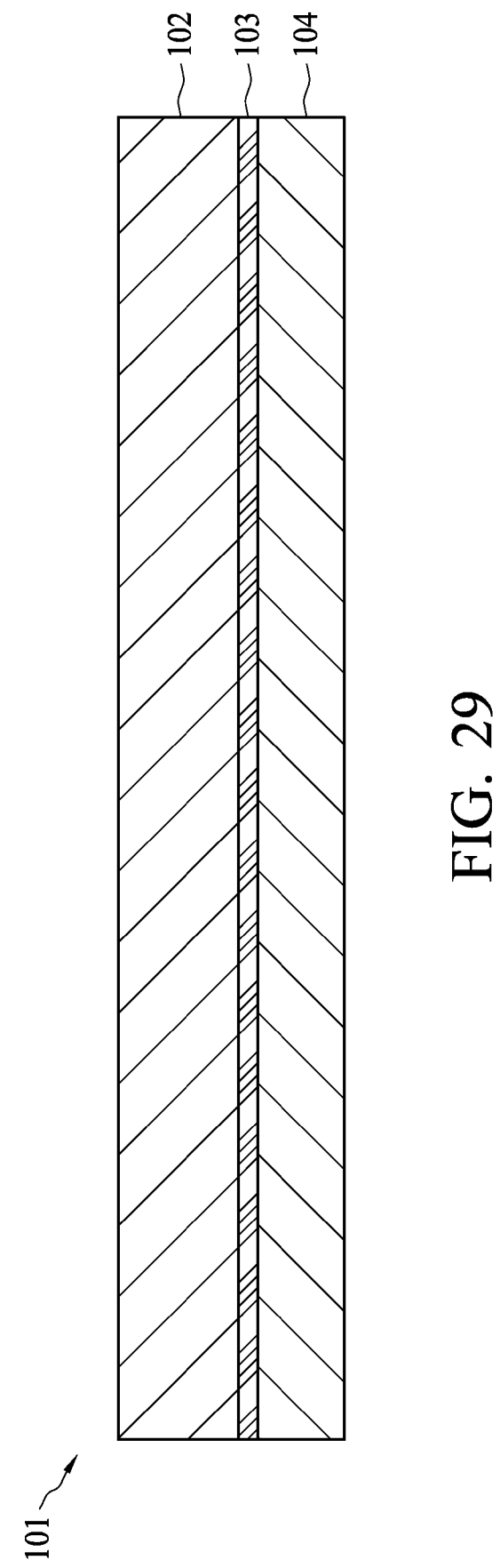

In the step 1010, a SOI wafer 101 is provided as shown in FIG. 29. The SOI wafer 101 includes a device layer 102, an electrical insulation layer 103 (made of $SiO_2$ in the embodiment) and a handle layer 104. Furthermore, the electrical insulation layer 103 is disposed between the device layer 102 and the handle layer 104.

Figure 30:
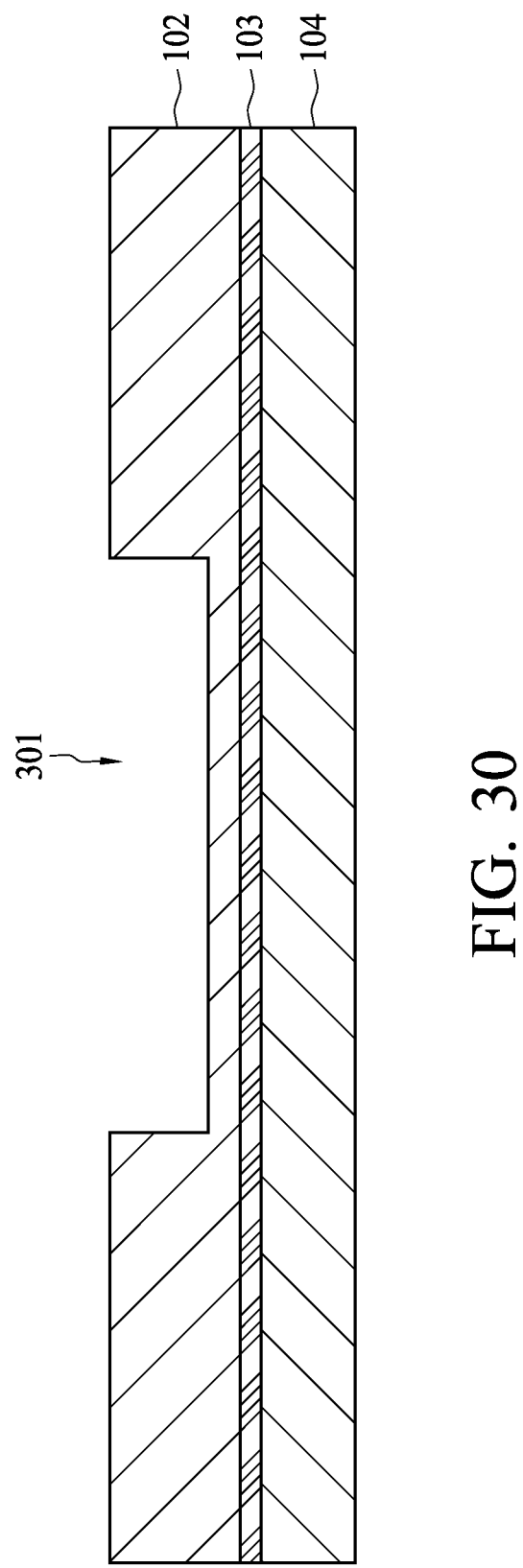

In the step 1020, the device layer 102 is etched to form recession 301 as shown in FIG. 30. In this step, the etching process is a wet etching (KOH etching).

Figure 31:
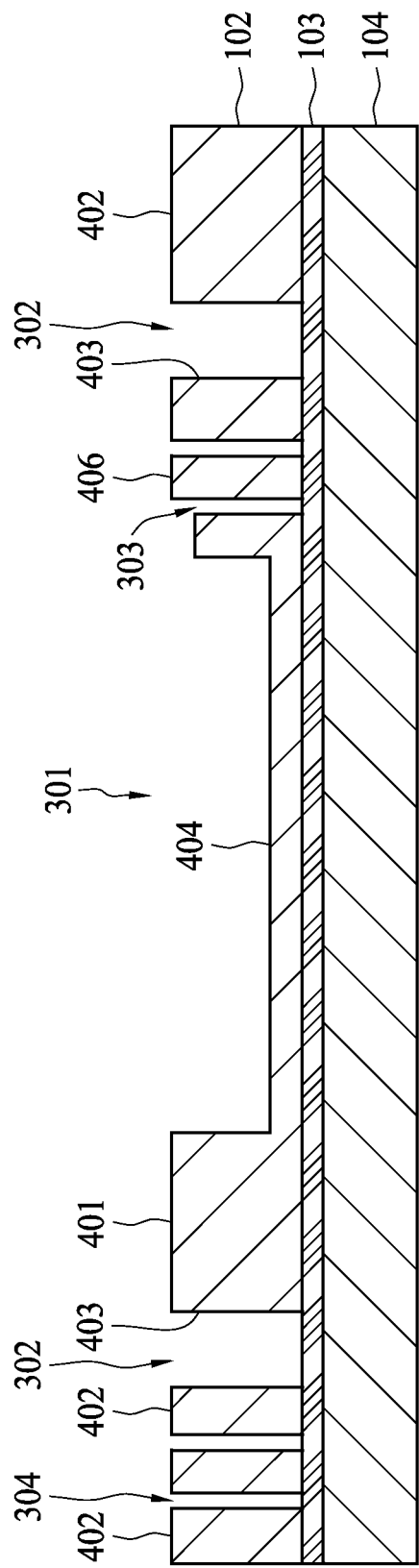

In the step 1020, the device layer 102 having the recession is etched to form a plurality of slots 302, 303 and 304 which expose the electrical insulation layer 103 as shown in FIG. 31. These slots 302, 303 and 304 and the recession 301 define the second electrode 401 and the third electrode 402 in the device layer 102. The second electrode 401 includes a sensing portion 404 and a stationary portion 403. In this step, the etching process is a dry etching such as Deep Reactive Ion Etching (Deep RIE).

As shown in FIG. 31, the slot 302 is configured for the stationary portion 403 to form a plurality of first protruding portions 234 shown in FIG. 7 and for the third electrode 402 to form a plurality of second protruding portions 241 shown in FIG. 7. In addition, the first protruding portions 234 and the second protruding portions 241 are arranged to form an interdigital capacitor.

In the embodiment, the etching step 1020 for the device layer 102 further includes a step of etching the stationary portion 403 to form a slot 303 exposing the electrical insulation layer 103. The slot 303 will form a through hole and the conductive post 406. The conductive post 406 is disposed inside the slot 303. Thus, the conductive post 406 is electrically insulated from the stationary portion 403.

Figure 32:
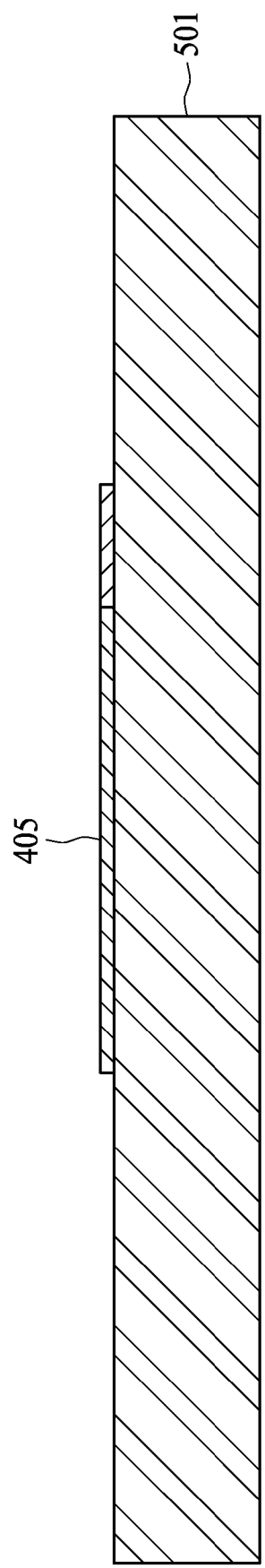

In the step 1030, the substrate wafer 501 is provided as shown in FIG. 32 and the first electrode 405 is disposed on the substrate wafer 501.

In the step 1040, the SOI wafer 101 and the substrate wafer 501 is bonded through wafer-to-wafer bonding process. This step allows the second electrode 401 and the third electrode 402 to be bonded on the top surface 502 of the substrate wafer 501. In this step, a wafer-to-wafer anodic bonding process is implemented. In the embodiment, the stationary portion 404 faces the first electrode 405, while the stationary portion 403 faces the third electrode 402. In addition, included angle between the pointing direction $N_2$ of the third electrode 402 and the pointing direction $N_1$ of the first electrode 405 is substantial 90°.

Figure 33:
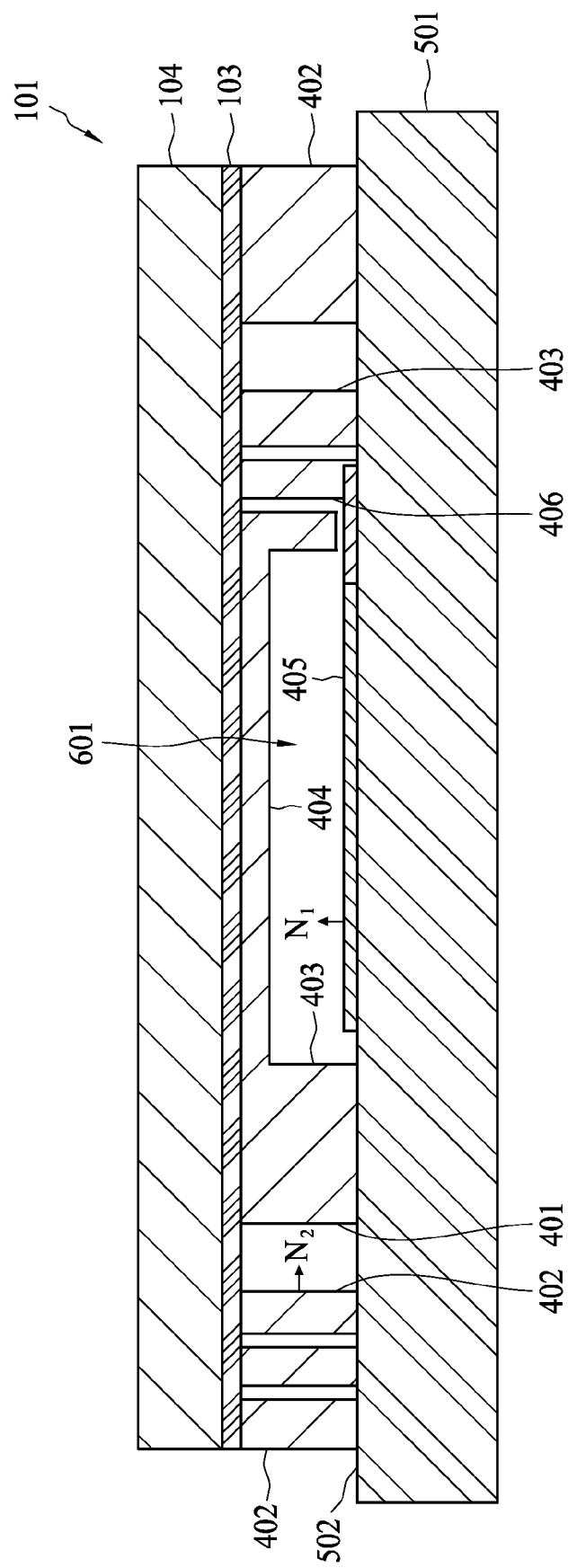

As shown in FIG. 33, one end of the stationary portion 403 is disposed on the top surface 502 of the substrate 501 and the other end of the stationary portion 403 is connected with the periphery of the sensing portion. The second electrode 401 is configured to seal the first electrode 405. In some embodiments, the sensing portion 404 of the second electrode 401, the stationary portion 403, the electrical insulation layer 103 and the substrate 501 define the first space 601. In the embodiment, the first space 601 is a hermetic space, which encloses the first electrode 405.

Figure 34:
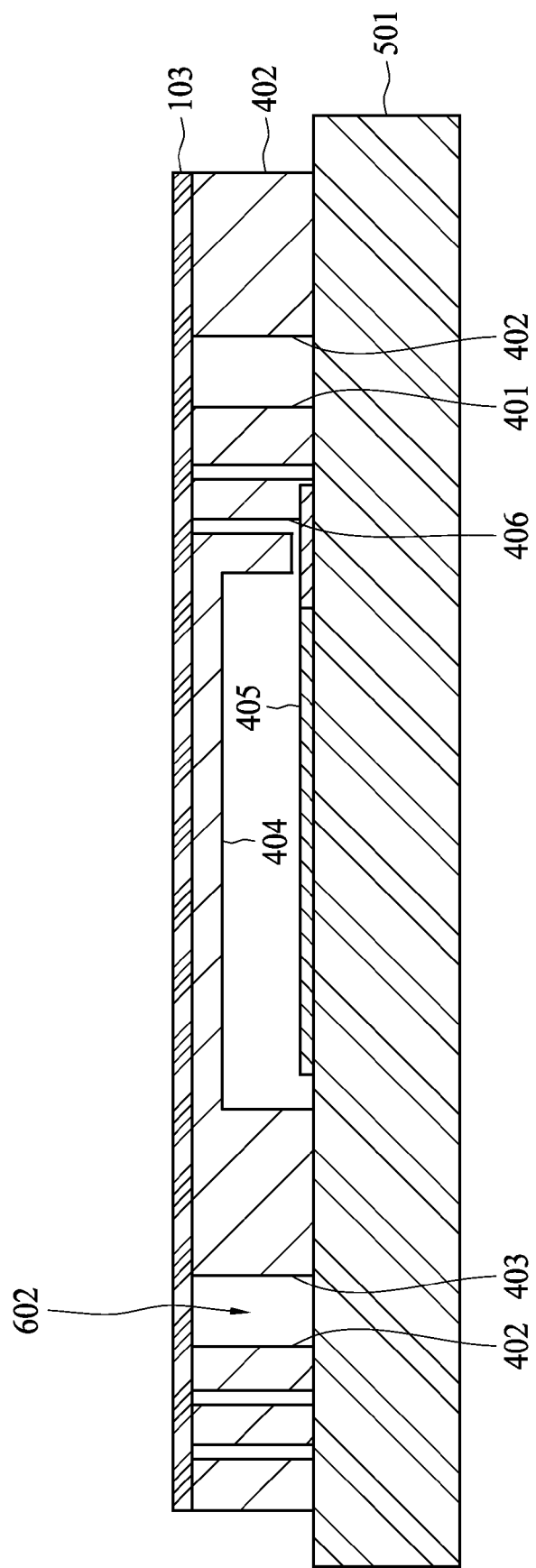

In the step 1050, the handle layer 103 shown in FIG. 33 is removed to complete the MEMS device shown in FIG. 34. In this step, the etching process is a wet etching such as KOH etching.

As shown in FIG. 34, the electrical insulation layer 103 covers the second electrode 401 and the third electrode 402. In addition, the electrical insulation 103, the stationary portion 403, the third electrode 402 and the substrate 501 define the second space 602. In the embodiment, the second space 602 is a hermetic space.

Figure 35:
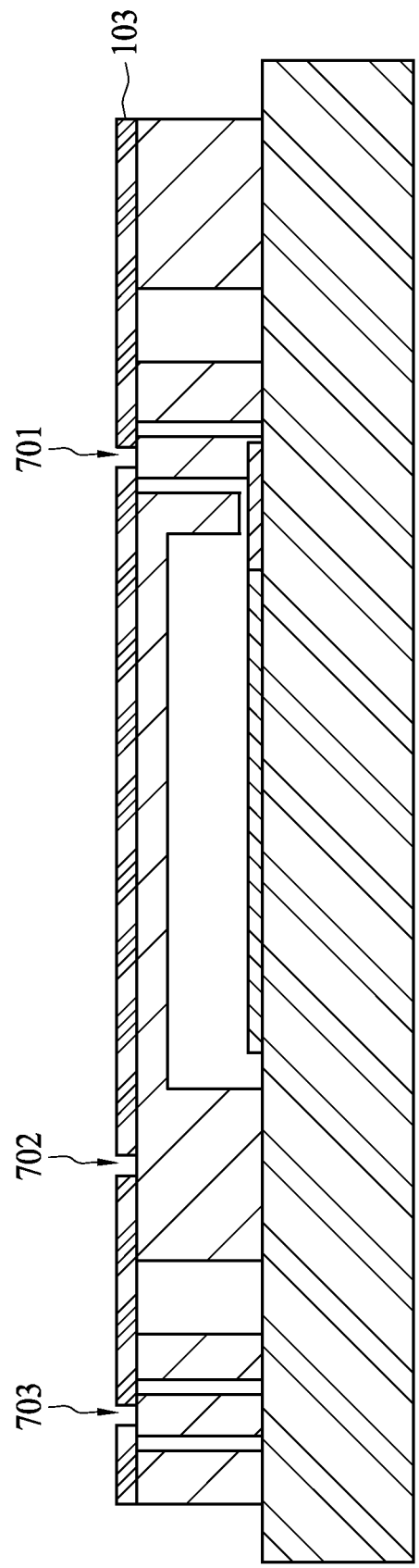
Figure 36:
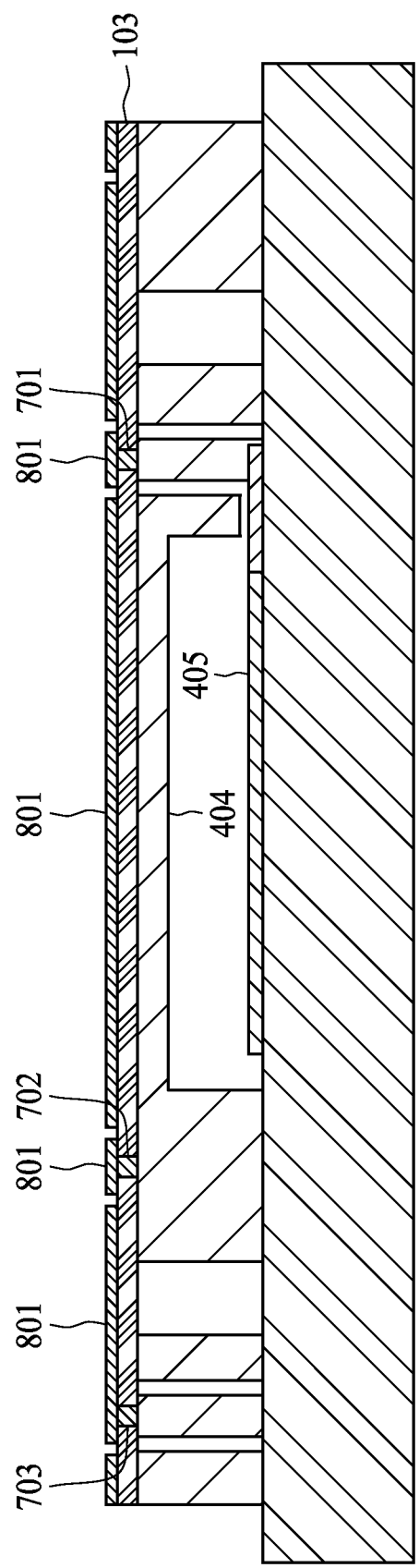
Figure 37:
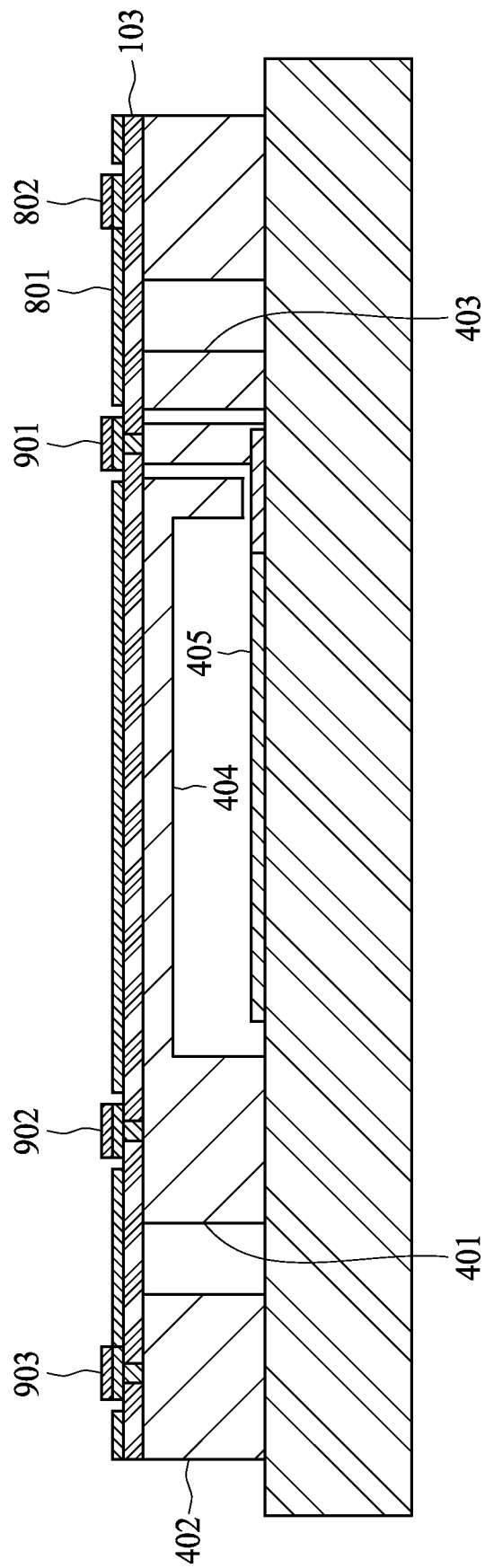

In addition, the fabricating method for the MEMS device shown in FIG. 28 may further include one of the following steps or a combination thereof so as to form the structures shown in FIGS. 35 to 37.

In the step 1060, the electrical insulation layer 103 may be further etched to form at least one openings 701, 702 and 703 as shown in FIG. 35. In this step, the etching process is a dry etching such as Reactive Ion Etching (RIE).

In the step 1070, the first conductive layer 801 is deposited on the electrical insulation layer 103 and is deposited in the openings 701, 702 and 703 as shown in FIG. 36. In this step, the depositing process is a metal depositing process such as metal deposition-aluminium process.

In the step 1080, the deposited conductive layer 802 is deposited on the first conductive layer 801 to form at least one electrical contacts 901, 902 and 903. The electrical contacts 901, 902 and 903 are electrically coupled to the first electrode 405, the second electrode 401 and the third electrode 402, respectively. In this step, the depositing process is a metal depositing process such as metal deposition-aluminium process.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, and composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A MEMS device with multiple electrodes, being adapted to sense air pressure, comprising:
   a substrate;
   a first electrode on the substrate;
   a second electrode on the substrate, including a sensing portion and a stationary portion; and
   a third electrode on the substrate, wherein when the sensing portion deforms, the stationary portion and the third electrode are spaced apart by a predetermined constant distance,
   wherein a stationary capacitor is defined between the stationary portion and the third electrode.

2. The MEMS device according to claim 1, wherein a sensing capacitor is defined between the sensing portion and the first electrode.

3. The MEMS device according to claim 1, wherein the first electrode is disposed on a top surface of the substrate, the stationary portion surrounds the first electrode, and the third electrode surrounds the second electrode.

4. The MEMS device according to claim 3, wherein one end of the stationary portion is disposed on the top surface of the substrate and the other end of the stationary portion connects a periphery of the sensing portion, a first space is defined between the second electrode and the substrate, and the first space is a hermetic space, which encloses the first electrode.

5. The MEMS device according to claim 4, further comprising an electrical insulation layer connecting the sensing portion and the third electrode, wherein the electrical insulation layer, the stationary portion, the third electrode and the substrate define a second space which is a hermetic space.

6. The MEMS device according to claim 4, further comprising a conductive post, wherein the stationary portion includes a through hole, the conductive post is disposed inside the through hole and is electrically coupled to the first electrode, and the conductive post is electrically insulated from the stationary portion.

7. The MEMS device according to claim 6, wherein the electrical insulation layer includes a first conductive through hole and a second conductive through hole, the first conductive through hole connects with the conductive post, and the second conductive through hole is electrically coupled to the second electrode.

8. A MEMS device with multiple electrodes, being adapted to sense air pressure, comprising:
a substrate;
a first electrode on the substrate;
a second electrode configured to define a sensing capacitor between the first electrode and the second electrode; and
a third electrode on the substrate, configured to define a stationary capacitor;
wherein the third electrode disconnects from the second electrode or the third electrode disconnects from the first electrode, a pointing direction of the first electrode is in parallel with a normal direction of the substrate, a pointing direction of the third electrode is perpendicular to the pointing direction of the first electrode.

9. The MEMS device according to claim 8, wherein the second electrode further includes a sensing portion, a deforming direction of the sensing portion is in parallel with the normal direction of the substrate.

10. The MEMS device according to claim 8, wherein the first electrode is disposed on a top surface of the substrate, the second electrode includes a sensing portion and a stationary portion, the stationary portion surrounds the first electrode, and the third electrode surrounds the stationary portion.

11. The MEMS device according to claim 10, wherein one end of the stationary portion is disposed on the top surface of the substrate and the other end of the stationary portion connects a periphery of the sensing portion, a first space is defined between the second electrode and the substrate, the first space is a hermetic space which encloses the first electrode.

12. The MEMS device according to claim 11, further comprising an electrical insulation layer connecting the sensing portion and the third electrode, wherein the electrical insulation layer, the stationary portion, the third electrode and the substrate define a second space which is a hermetic space.

13. The MEMS device according to claim 11, further comprising a conductive post, wherein the stationary portion includes a through hole, the conductive post is disposed inside the through hole and is electrically coupled to the first electrode, and the conductive post is electrically insulated from the stationary portion.

14. The MEMS device according to claim 13, wherein the electrical insulation layer includes a first conductive through hole and a second conductive through hole, the first conductive through hole connects with the conductive post, and the second conductive through hole is electrically coupled to the second electrode.

15. A MEMS device with multiple electrodes, comprising:
a substrate;
a first electrode on the substrate, wherein a pointing direction of the first electrode is in parallel with the normal direction of the substrate;
a second electrode on the substrate, including a sensing portion and a stationary portion; and
a third electrode on the substrate, wherein a pointing direction of the third electrode is perpendicular to the pointing direction of the first electrode;
wherein the sensing portion faces the first electrode, the stationary portion faces the third electrode, when the sensing portion deforms, the stationary portion and the third electrodes are spaced apart by a predetermined constant distance.

16. The MEMS device according to claim 15, wherein a deforming direction of the sensing portion is in parallel with the normal direction of the substrate.

17. The MEMS device according to claim 15, wherein the first electrode is disposed on a top surface of the substrate, the stationary portion surrounds the first electrode, the third electrode surrounds the stationary portion, the sensing portion and the first electrode are spaced apart by a gap.

18. The MEMS device according to claim 17, wherein the stationary portion includes a plurality of first protruding portions, and the third electrode includes a plurality of second protruding portions, wherein the first protruding portions and the second protruding portions are arranged to form an interdigital capacitor.

19. The MEMS device according to claim 17, wherein one end of the stationary portion is disposed on the top surface of the substrate and the other end of the stationary portion connects the sensing portion.

20. The MEMS device according to claim 19, wherein the sensing portion, the stationary portion and the substrate define a first space which encloses the first electrode.

21. The MEMS device according to claim 20, wherein the first space is a hermetic space.

22. The MEMS device according to claim 20, further comprising an electrical insulation layer connecting the second electrode and the third electrode, wherein the electrical insulation layer, the stationary portion, the third electrode and the substrate define a second space.

23. The MEMS device according to claim 22, wherein the second space is a hermetic space.

24. The MEMS device according to claim 19, further comprising a conductive post, wherein the stationary portion includes a through hole, the conductive post is disposed inside the through hole and is electrically coupled to the first electrode, and the conductive post is electrically insulated from the stationary portion.

25. The MEMS device according to claim 19, further comprising an electrical insulation layer connecting the second electrode and the third electrode, wherein the electrical insulation layer, the stationary portion, the third electrode and the substrate define a second space, and the electrical insulation layer covers the partial sensing portion.

26. The MEMS device according to claim 22, further comprising a first conductive layer disposed on the electrical insulation layer.

27. The MEMS device according to claim 25, further comprising a second conductive layer disposed on the sensing portion which is not covered by the electrical insulation layer.

28. The MEMS device according to claim 24, further comprising an integrated circuit chip, wherein the material of the substrate is made of glass, the integrated circuit chip is disposed on a bottom surface of the substrate, and the integrated circuit chip is electrically coupled to the conductive post.

29. The MEMS device according to claim 24, further comprising a first conductive post, an external conductive trace, an electrical isolation layer, a conductive trace layer, a conductive bump, and a conductive trace, wherein, the first conductive post is disposed inside the third electrode, the first conductive post is electrically insulated from the third electrode, the electrical insulation layer includes a first conductive through hole and a second conductive through hole, the external conductive trace is disposed on the electrical insulation layer, the electrical isolation layer is disposed on a bottom surface of the third electrode, the electrical isolation layer includes a third conductive through hole, the conductive trace layer is disposed below the electrical isolation layer, the partial conductive trace layer is disposed between the electrical isolation layer and the substrate, the conductive bump is disposed on the integrated circuit chip, the first conductive through hole of the electrical insulation layer connects the conductive post to the external conductive trace, the second conductive through hole of the electrical insulation layer connects the external conductive trace to the first conductive post, the third conductive through hole of the electrical isolation layer connects the first conductive post to the conductive trace layer, and the conductive wire connects the conductive trace layer and the conductive bump.

30. The MEMS device according to claim 24, wherein the electrical insulation layer includes a first conductive through hole and a second conductive through hole, the first conductive through hole connects with the conductive post, and the second conductive through hole is electrically coupled to the second electrode.

31. The MEMS device according to claim 24, wherein the substrate is an integrated circuit chip further including at least one conductive through hole, wherein the at least one conductive through hole is configured to allow the first electrode, the second electrode and the third electrode to be electrically coupled to at least one conductive bump of the integrated circuit chip, respectively.

32. The MEMS device according to claim 31, further comprising a second conductive post, wherein a conductive layer is disposed on the electrical insulation layer, the second conductive post is disposed inside the third electrode and is electrically insulated from the third electrode, and the at least one conductive through hole is electrically coupled to the conductive layer through the conductive post.

33. The MEMS device according to claim 22, wherein the substrate includes at least one opening and a back chamber, wherein the at least one opening communicates with the second space, the back chamber is disposed under the first electrode, and the first electrode further includes a plurality of apertures by which the back chamber communicates with the first space.

34. The MEMS device according to claim 20, further comprising a dielectric material which is disposed in the first space and is disposed between the stationary portion and the third electrode.

35. A fabricating method of a MEMS device with multiple electrodes, the method comprising the following steps:
providing a Silicon On Insulator (SOI) wafer, wherein the SOI wafer includes a device layer, an electrical insulation layer and a handle layer, wherein the electrical insulation layer is disposed between the device layer and the handle layer;
etching the device layer to form a recession;
etching the device layer having the recession to form a plurality of slots which expose the electrical insulation layer and to form a through hole which exposes the electrical insulation layer, wherein the slots and the recession define a second electrode which includes a sensing portion and a stationary portion, the through hole is disposed in the stationary portion, the slots also define a third electrode and a conductive post which is disposed inside the through hole and is electrically insulated from the stationary portion;
providing a substrate wafer on which a first electrode is disposed;
bonding the SOI wafer and the substrate wafer through wafer-to-wafer bonding to allow the second electrode and the third electrode to connect to a top surface of the substrate wafer, wherein the sensing portion faces the first electrode, the stationary portion faces the third electrode, a pointing direction of the third electrode is perpendicular to a pointing direction of the first electrode, the stationary portion and the third electrode are spaced apart by a predetermined constant distance, the second electrode and the third electrode are disposed on the substrate wafer, and the stationary portion and the third electrode is configured to define a stationary capacitor; and
removing the handle layer.

36. The fabricating method according to claim 35, wherein the slots are configured for the stationary portion to form a plurality of first protruding portions and are configured for the third electrode to form a plurality of second protruding portions, and the first protruding portions and the second protruding portions are arranged to form an interdigital capacitor.

37. The fabricating method according to claim 35, wherein one end of the stationary portion is disposed on the top surface of the substrate and the other end of the stationary portion connects a periphery of the sensing portion, the second electrode is configured to seal the first electrode, the sensing portion, the stationary portion, the electrical insulation layer and the substrate define a first space, and the first space is a hermetic space.

38. The fabricating method according to claim 35, wherein the electrical insulation layer covers the second electrode and the third electrode, the electrical insulation layer, the stationary portion, the third electrode and the substrate define a second space, and the second space is a hermetic space.

39. The fabricating method according to claim 35, further comprising one of the following steps or a combination thereof:
etching the electrical insulation layer to form at least one opening;
depositing a first conductive layer on the electrical insulation layer; and
depositing a deposited conductive layer on the first conductive layer to form at least one electrical contact.

* * * * *